United States Patent
Abdou

(10) Patent No.: US 7,909,871 B2
(45) Date of Patent: Mar. 22, 2011

(54) DEVICES AND METHODS FOR INTER-VERTEBRAL ORTHOPEDIC DEVICE PLACEMENT

(76) Inventor: Samy Abdou, San Diego, CA (US)

( * ) Notice: Subject to any disclaimer, the term of this patent is extended or adjusted under 35 U.S.C. 154(b) by 802 days.

(21) Appl. No.: 11/543,012

(22) Filed: Oct. 3, 2006

(65) Prior Publication Data
US 2007/0106383 A1    May 10, 2007

Related U.S. Application Data

(60) Provisional application No. 60/723,185, filed on Oct. 3, 2005, provisional application No. 60/809,199, filed on May 30, 2006.

(51) Int. Cl.
*A61F 2/44* (2006.01)
*A61B 17/70* (2006.01)
*A61B 17/88* (2006.01)

(52) U.S. Cl. ............... 623/17.11; 623/17.12; 623/17.13; 623/17.14; 623/17.15; 623/17.16; 606/60; 606/246; 606/257; 606/264; 606/265; 606/279

(58) Field of Classification Search .... 623/17.11–17.16; 606/60, 246, 257, 264–265, 279
See application file for complete search history.

(56) References Cited

U.S. PATENT DOCUMENTS

| | | | |
|---|---|---|---|
| 2,248,054 A | 7/1941 | Becker | |
| 3,659,595 A | 5/1972 | Haboush | |
| 4,790,303 A * | 12/1988 | Steffee | 606/300 |
| 4,903,692 A | 2/1990 | Reese | |
| 5,275,601 A | 1/1994 | Gogolewski et al. | |
| 5,354,292 A | 10/1994 | Braeuer et al. | |
| 5,360,429 A | 11/1994 | Jeanson et al. | |
| 5,484,440 A | 1/1996 | Allard | |
| 5,531,747 A | 7/1996 | Ray | |

(Continued)

FOREIGN PATENT DOCUMENTS
EP    1180348    2/2002
(Continued)

OTHER PUBLICATIONS

Derwent English abstract for FR2781359, published Jan. 28, 2000 entitled: "Osteosynthesis frame for spinal surgery has rod with clamps to hold cross bars with anchor screws," Accession No. 9867555 [351].

(Continued)

*Primary Examiner* — Thomas C Barrett
*Assistant Examiner* — Sameh Boles
(74) *Attorney, Agent, or Firm* — Fred C. Hernandez; Mintz Levin Cohn Ferris Glovsky and Popeo P.C.

(57) ABSTRACT

Disclosed are devices and methods for the placement of a bone fusion implant between vertebral bodies in a human or animal subject. In an exemplary method a pathway is formed in the first sacral vertebrae along a trajectory that has a starting point between the inferior aspect of the facet joint and the first posterior sacral foramen and transverses at least one pedicle, at least a portion of the first sacral vertebra and the disc space immediately superior to the sacrum. A fusion implant is placed into the formed pathway. Additional bone fasteners and inter-connecting rods are added to the fusion implant in order to further strengthen the construct. Embodiments that can be used to fuse an additional level are also disclosed.

58 Claims, 18 Drawing Sheets

U.S. PATENT DOCUMENTS

| | | | |
|---|---|---|---|
| 5,545,164 | A | 8/1996 | Howland |
| 5,558,674 | A | 9/1996 | Heggeness et al. |
| 5,616,142 | A | 4/1997 | Yuan et al. |
| 5,672,176 | A | 9/1997 | Biedermann et al. |
| 5,681,312 | A | 10/1997 | Yuan et al. |
| 5,971,987 | A | 10/1999 | Huxel et al. |
| 5,993,449 | A | 11/1999 | Schlapfer et al. |
| 6,059,786 | A | 5/2000 | Jackson |
| 6,086,589 | A * | 7/2000 | Kuslich et al. ............... 606/247 |
| 6,117,135 | A | 9/2000 | Schlapfer |
| 6,139,549 | A | 10/2000 | Keller |
| 6,159,244 | A | 12/2000 | Suddaby |
| 6,306,136 | B1 | 10/2001 | Baccelli |
| 6,309,391 | B1 | 10/2001 | Crandall et al. |
| 6,331,179 | B1 | 12/2001 | Freid et al. |
| 6,402,752 | B2 | 6/2002 | Schaffler-Wachter et al. |
| 6,432,140 | B1 * | 8/2002 | Lin ............................ 623/17.16 |
| 6,530,929 | B1 | 3/2003 | Justis et al. |
| 6,558,386 | B1 | 5/2003 | Cragg |
| 6,558,390 | B2 | 5/2003 | Cragg |
| 6,599,294 | B2 | 7/2003 | Fuss et al. |
| 6,599,295 | B1 | 7/2003 | Tornier et al. |
| 6,645,207 | B2 | 11/2003 | Dixon et al. |
| 6,663,631 | B2 | 12/2003 | Kuntz |
| 6,716,212 | B1 | 4/2004 | Pickens |
| 6,730,126 | B2 | 5/2004 | Boehm, Jr. et al. |
| 6,740,090 | B1 | 5/2004 | Cragg et al. |
| 6,749,614 | B2 | 6/2004 | Teitelbaum et al. |
| 6,783,547 | B2 | 8/2004 | Castro |
| 6,790,210 | B1 | 9/2004 | Cragg et al. |
| 6,805,697 | B1 | 10/2004 | Helm et al. |
| 6,821,277 | B2 | 11/2004 | Teitelbaum |
| 6,830,571 | B2 | 12/2004 | Lenke et al. |
| 6,885,243 | B2 | 4/2005 | Burstein et al. |
| 6,899,716 | B2 | 5/2005 | Cragg |
| 6,921,403 | B2 | 7/2005 | Cragg et al. |
| 7,014,633 | B2 | 3/2006 | Cragg |
| 7,060,066 | B2 * | 6/2006 | Zhao et al. ..................... 606/279 |
| 7,087,058 | B2 | 8/2006 | Cragg |
| 2002/0016595 | A1 | 2/2002 | Michelson |
| 2002/0055741 | A1 | 5/2002 | Schlapfer et al. |
| 2002/0099386 | A1 | 7/2002 | Berger et al. |
| 2002/0143328 | A1 | 10/2002 | Shulzas et al. |
| 2002/0183755 | A1 | 12/2002 | Michelson |
| 2002/0188296 | A1 | 12/2002 | Michelson |
| 2003/0018389 | A1 | 1/2003 | Castro et al. |
| 2003/0078583 | A1 | 4/2003 | Biedermann et al. |
| 2003/0153913 | A1 | 8/2003 | Altarac et al. |
| 2003/0229347 | A1 | 12/2003 | Sherman et al. |
| 2004/0073216 | A1 * | 4/2004 | Lieberman ..................... 606/61 |
| 2004/0133207 | A1 | 7/2004 | Abdou |
| 2004/0153070 | A1 | 8/2004 | Barker et al. |
| 2004/0204712 | A1 | 10/2004 | Kolb et al. |
| 2004/0204713 | A1 | 10/2004 | Abdou |
| 2005/0004573 | A1 | 1/2005 | Abdou |
| 2005/0010227 | A1 | 1/2005 | Paul |
| 2005/0021040 | A1 | 1/2005 | Bertagnoli |
| 2005/0119747 | A1 | 6/2005 | Fabris Monterumici et al. |
| 2005/0131406 | A1 * | 6/2005 | Reiley et al. ..................... 606/61 |
| 2005/0177163 | A1 | 8/2005 | Abdou |
| 2005/0273120 | A1 | 12/2005 | Abdou |
| 2005/0283153 | A1 | 12/2005 | Poyner et al. |
| 2005/0288669 | A1 | 12/2005 | Abdou |
| 2006/0074488 | A1 | 4/2006 | Abdou |
| 2006/0149278 | A1 | 7/2006 | Abdou |
| 2006/0217710 | A1 | 9/2006 | Abdou |
| 2006/0229615 | A1 | 10/2006 | Abdou |
| 2007/0093828 | A1 | 4/2007 | Abdou |
| 2007/0123884 | A1 | 5/2007 | Abdou |

FOREIGN PATENT DOCUMENTS

| | | |
|---|---|---|
| FR | 2781359 | 1/2000 |
| FR | 2856271 | 12/2004 |
| WO | 2004/032726 | 4/2004 |
| WO | 2004/062482 | 7/2004 |
| WO | 2004/093702 | 11/2004 |
| WO | 2005/122922 | 12/2005 |
| WO | 2006/041963 | 4/2006 |
| WO | 2006/058221 | 6/2006 |
| WO | 2006/089292 | 8/2006 |
| WO | 2006/096756 | 9/2006 |
| WO | WO 2007/041648 | 4/2007 |
| WO | WO 2007/044705 | 4/2007 |
| WO | WO 2007/044836 | 4/2007 |
| WO | WO 2007/056516 | 5/2007 |
| WO | WO 2007/059207 | 5/2007 |

OTHER PUBLICATIONS

Derwent English abstract for FR2856271, published Dec. 24, 2004 entitled: "Osteo-synthesis vertebral column plate, has connection head integrated with plate and moveable in three directions of space so as to adapt itself to connection rod, and including opening to facilitate introduction of rod," Accession No. 14694557 [351].

* cited by examiner

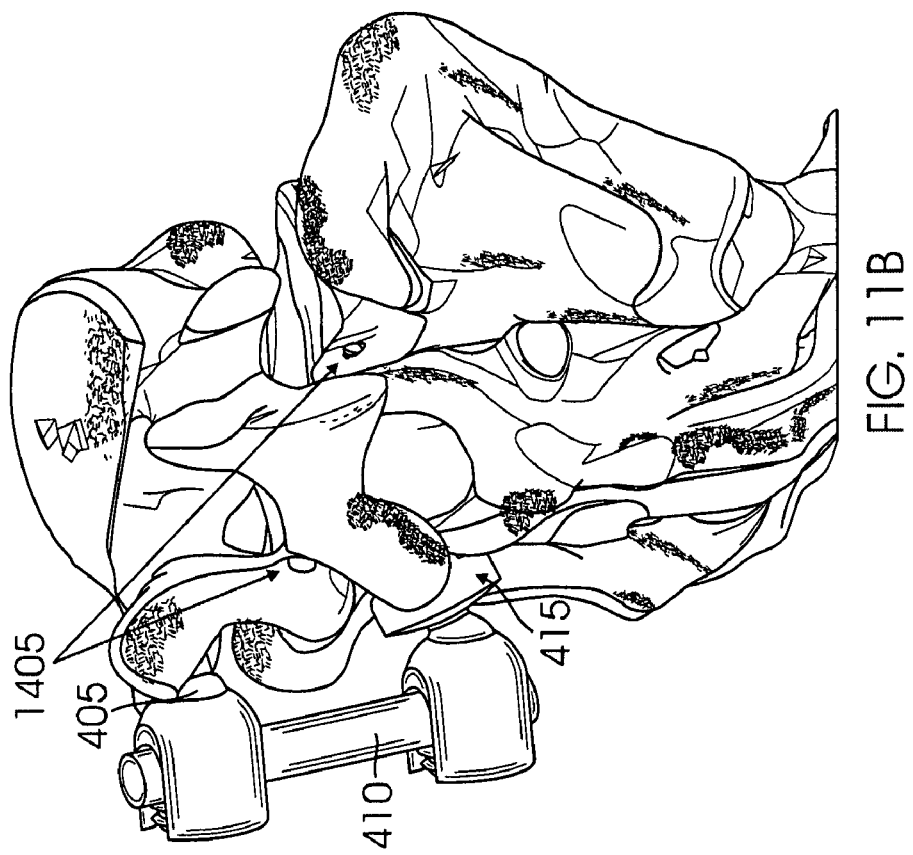
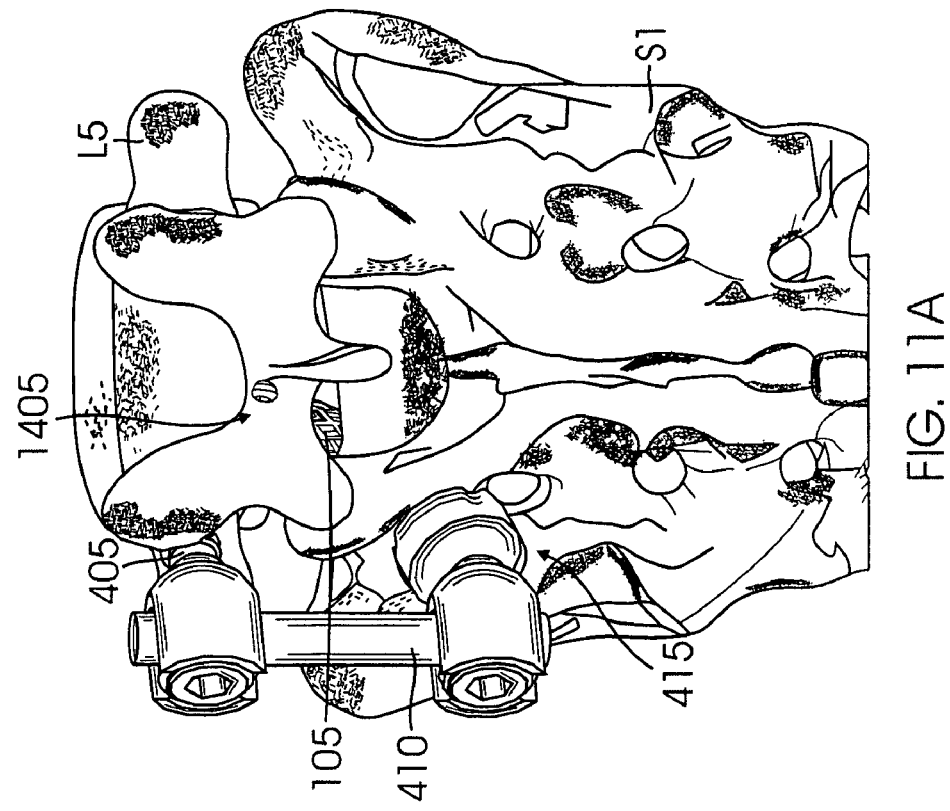

DEVICES AND METHODS FOR INTER-VERTEBRAL ORTHOPEDIC DEVICE PLACEMENT

RELATED APPLICATIONS

This application claims priority of U.S. Provisional Patent Application Ser. No. 60/723,185 entitled "Device for the Stabilization of the Low Lumbar Spine and Method of Use" by M. S. Abdou, filed Oct. 3, 2005 and U.S. Provisional Patent Application Ser. No. 60/809,199, filed May 30, 2006. Priority of the aforementioned filing dates is hereby claimed and the disclosures of the Provisional Patent Applications are hereby incorporated by reference in their entirety.

This application also is related to International application Serial No. PCT/US2006/38865, filed the same day herewith.

Where permitted, the subject matter of each of the above noted provisional applications, and international application is incorporated by reference in its entirety by reference thereto.

BACKGROUND

The present disclosure relates to methods and devices that permit stabilization of the bony elements of the skeleton. The devices permit adjustment and maintenance of the spatial relationship(s) between neighboring bones. Depending on the specifics of the design, the motion between skeletal segments can be immobilized completely or preserved.

Surgical reconstructions of the bony skeleton are common procedures in current medical practice. Regardless of the anatomical region or the specifics of the reconstructive procedure, many surgeons employ an implantable device that can adjust, align and maintain the spatial relationship(s) between adjacent bones.

Whether from degenerative disease, traumatic disruption, infection or neoplastic invasion, alteration in the anatomical relationships between the spinal vertebrae can cause significant pain, deformity and disability. Spinal disease is a major health problem in the industrialized world and the surgical treatment of spinal pathology is an evolving discipline. The current surgical treatment of abnormal vertebral motion is the complete immobilization and bony fusion of the involved spinal segment. An extensive array of surgical techniques and implantable devices has been formulated to accomplish this goal. More recently, alternative techniques have been developed to correct the abnormal vertebral motion and preserve spinal mobility.

Symptomatic degeneration of the lumbar spine occurs most commonly at the L4/L5 and L5/S1 levels. Fusion of one or both of these segments has emerged as a common surgical procedure. Currently, these vertebral bodies can be fused using an anterior, lateral or posterior approach and each has particular advantages and draw backs. Frequently, circumferential fusion of the unstable level with fixation of both the anterior and posterior aspect of the spine is desired. This requires that patients undergo a combination of the aforementioned approaches. The anterior or lateral approaches are used to insert the bone graft into the disc space between the adjacent vertebrae while the posterior approach is used to place bone screws or similar fasteners that are used to immobilize the vertebral bodies.

Currently, circumferential fusion requires a combination of approaches and multiple surgical incisions. A minimally invasive procedure that can provide circumferential access to the lower lumbar spine is clearly needed.

SUMMARY

Disclosed are devices and methods for providing circumferential lumbar fusion through a single approach. The method of use minimizes the dissection of normal tissues and avoids retraction and manipulation of the nerve elements. The method also provides ease of use as well as a safe and familiar surgical approach that maximizes the likelihood of optimal graft placement within the inter-vertebral disc space. The device can be placed through a posterior approach to the spine and thus avoids the risk of an intra-abdominal operation.

In one aspect, a bone screw is placed through the pedicle portion of the vertebral body immediately superior to the sacrum. This is usually, but not always, the L5 vertebral body. For simplicity, it will be assumed to be the L5 vertebral body and will be so designated for the remainder of the application. A curvilinear bone graft containment cage is advanced through the posterior portion of the sacrum, the sacral pedicle, the disc space immediately above the sacrum (designated the L5/S1 disc space) and onto or into the inferior aspect of the L5 vertebral body. A rod or similar connecting member is used to connect the L5 screw with the posterior aspect of the bone cage and/or sacral screw. The procedure can be performed unilaterally or, more preferably, bilaterally. Alternatively, the procedure can be used unilaterally in conjunction with additional methods of vertebral fixation. The latter include but are not limited to use of a facet-locking screw to fixate the contra-lateral facet joint or a device to fixate the spinous processes.

In additional embodiments, a shorter L5 bone screw is used and the cage is driven through the L5 vertebral body and L4/5 disc space and onto or into the inferior aspect of the L4 vertebral body. A rod or other connecting element is used to connect the L4 and L5 bone screws to the cage and/or onto an S1 bone screw. In this way, circumferential fixation of L4 to S1 is achieved. As before, the procedure can be performed unilaterally, bilaterally or in combination with other fixation techniques.

In other embodiments, the curvilinear device and/or approach through the sacrum is used to place a tissue graft, biological extracts or agents, nucleus replacement prosthesis or any desired material into the L5/S1 and/or L4/5 disc spaces. In a final embodiment, devices and methods are used to distract neighboring vertebral bodies.

The devices disclosed herein and the methods of placement provide an easy and reliable way for circumferential stabilization of the lower lumbar spine through a single approach. Depending on the use of the prosthesis, the disclosed device can be used to fuse the targeted vertebral bodies or as conduit for the placement of biologic or synthetic substances into the disc space(s). The disclosed method of implant use is safe; it employs a posterior approach that is familiar to all spine surgeons and the method minimizes the extent of dissection of the normal tissues.

A bone fusion implant is disclosed in which the implant is adapted to be positioned between vertebral bodies in a human or animal subject. In one embodiment, the bone fusion implant includes an elongate member. The elongate member is sized and shaped to be positioned within a pathway in the first sacral vertebra along a trajectory that has a starting point between a portion of the facet joint and the posterior sacral foramen, that transverses at least one sacral pedicle and at least a portion of the first sacral vertebral body and that enters the disc space immediately superior to the sacrum. In another embodiment, the implant includes a curvilinear member sized and shaped to be positioned within a curvilinear pathway that joins at least two vertebral bodies and at least partially contains a bone graft.

A method is disclosed for the placement of a bone fusion implant between vertebral bodies in a human or animal subject. The method includes placing an implant into a pathway formed in a first sacral vertebra along a trajectory that has a starting point between a portion of the facet joint and the posterior sacral foramen, transverses at least one sacral pedicle and at least a portion of the first sacral vertebral body and enters the disc space immediately superior to the sacrum.

A method is disclosed for the placement of a tissue graft, biological extracts or agents, nucleus replacement prosthesis or any desired material into disc space between vertebral bodies in a human or animal subject is disclosed. The method includes placing the material into the disc space through a pathway formed in the first sacral vertebra along a trajectory that has a starting point between a portion of the facet joint and the posterior sacral foramen, transverses at least one sacral pedicle and at least a portion of the first sacral vertebral body and enters the disc space immediately superior to the sacrum.

A method for vertebral movement in a human or animal subject is disclosed. The method includes forming a pathway in the first sacral vertebra along a trajectory that has a starting point between a portion of the facet joint and the posterior sacral foramen, transverses at least one sacral pedicle and at least a portion of the first sacral vertebral body and enters the disc space immediately superior to the sacrum; placing a first distraction member with a central opening through the pathway and into contact with a lower vertebral body to be moved; placing a second distraction member through the central opening of the first distraction member and into contact with an upper vertebral body to be moved; and applying a force so as to move and displace the first and second distraction members and the attached upper and lower vertebral bodies relative to one another.

Another method for vertebral movement in a human or animal subject is disclosed. The method includes forming a pathway in a first sacral vertebra along a trajectory that has a starting point between a portion of a facet joint and the posterior sacral foramen, transverses at least one sacral pedicle and at least a portion of the first sacral vertebral body and enters the disc space immediately superior to the sacrum; placing an implant into the formed pathway and into contact with a lower vertebral body to be moved; affixing a sacral attachment onto the sacrum; applying a force so as to move and displace the implant and sacral attachment and the attached upper and lower vertebral bodies relative to one another.

Another method of placing and positioning a fusion implant is disclosed. The method includes forming a curvilinear path within a first sacral vertebra wherein the pathway is centered about a point along a long axis of the L5 fastener placed into a pedicle portion of an L5 vertebral body. The path has a starting point between a portion of the facet joint and the posterior sacral foramen and transverses at least one sacral pedicle and at least a portion of the first sacral vertebral body and enters the disc space immediately superior to the sacrum. The method also includes positioning a fusion implant along the formed path.

Other features and advantages should be apparent from the following description of various embodiments, which illustrate, by way of example, the principles of the disclosed devices and methods.

BRIEF DESCRIPTION OF THE DRAWINGS

FIGS. 11A and 11B show a complete segmental fixation through a unilateral approach.

DETAILED DESCRIPTION

Figure 1B:
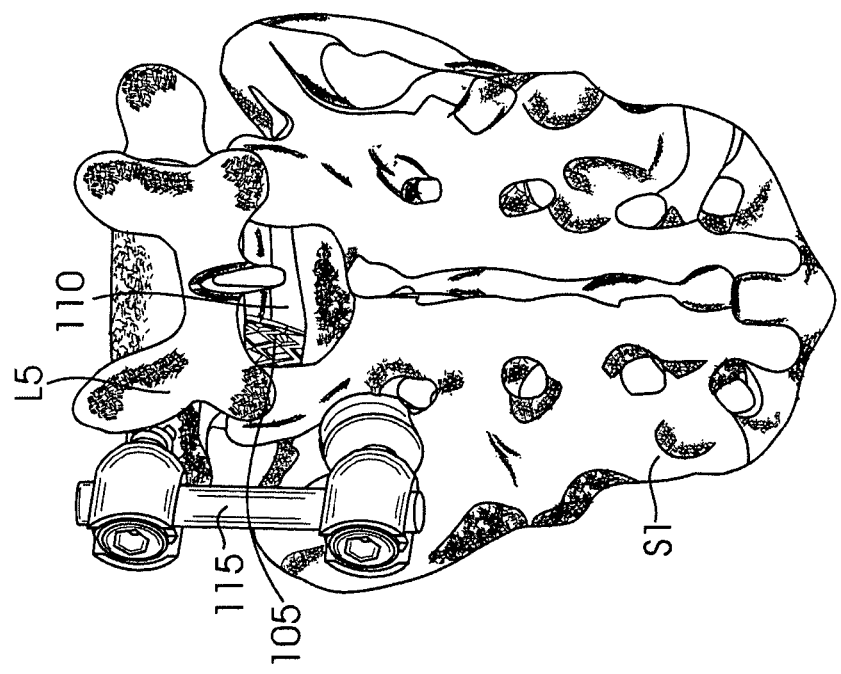
FIGS. 1A and 1B show side and posterior views of a bone screw implanted into the L5 vertebral body and a fusion implant positioned to transverse the sacral pedicle and the L5/S1 disc space.
Figure 1A:
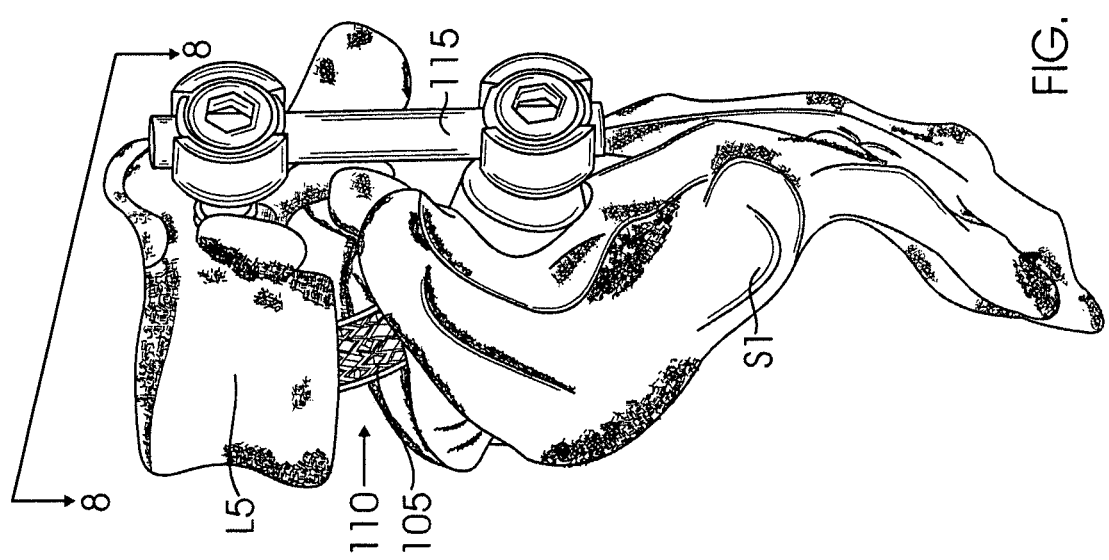
Figure 2:
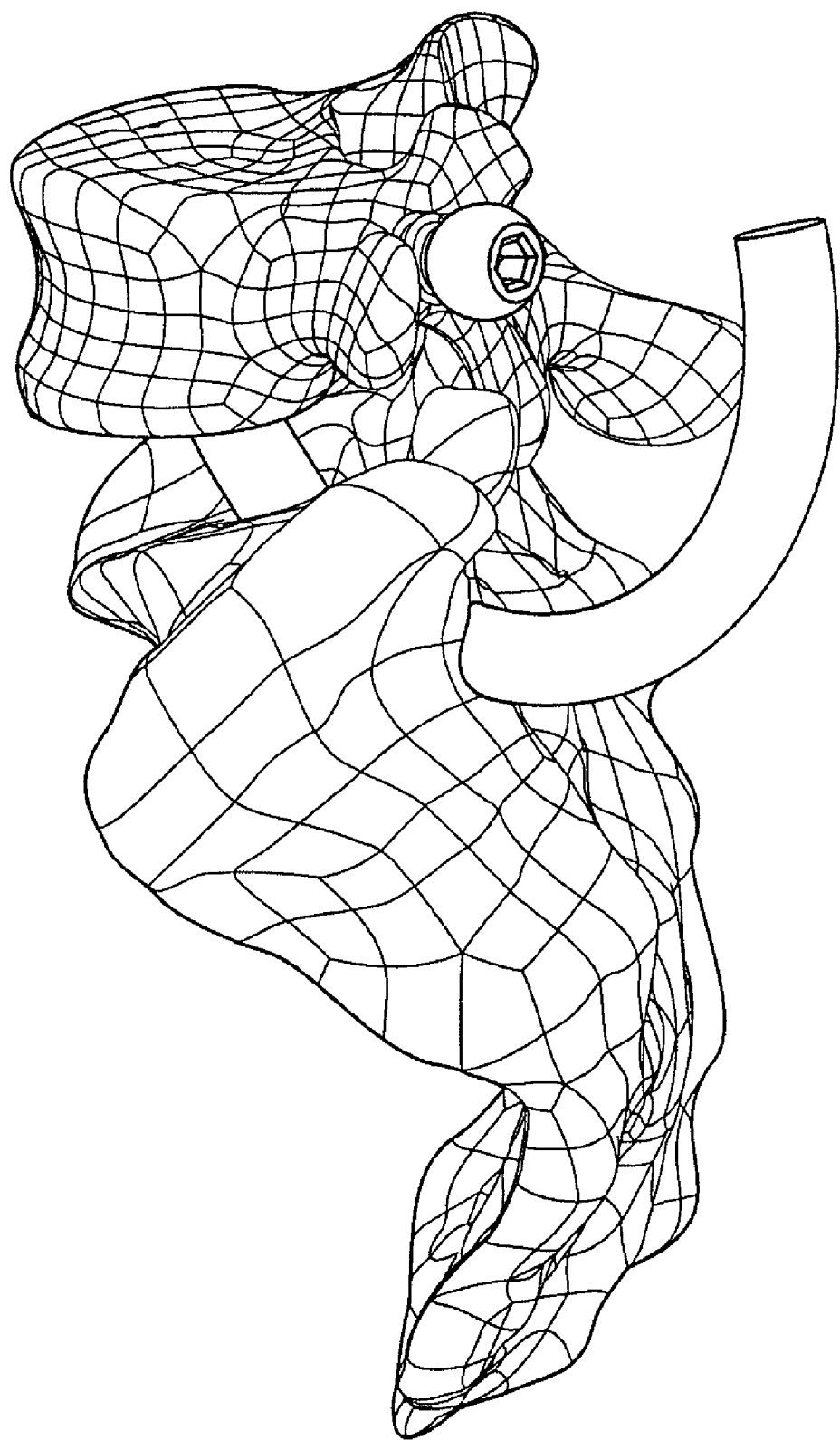
FIG. 2 shows the approximate path of an implant.
Figure 3:
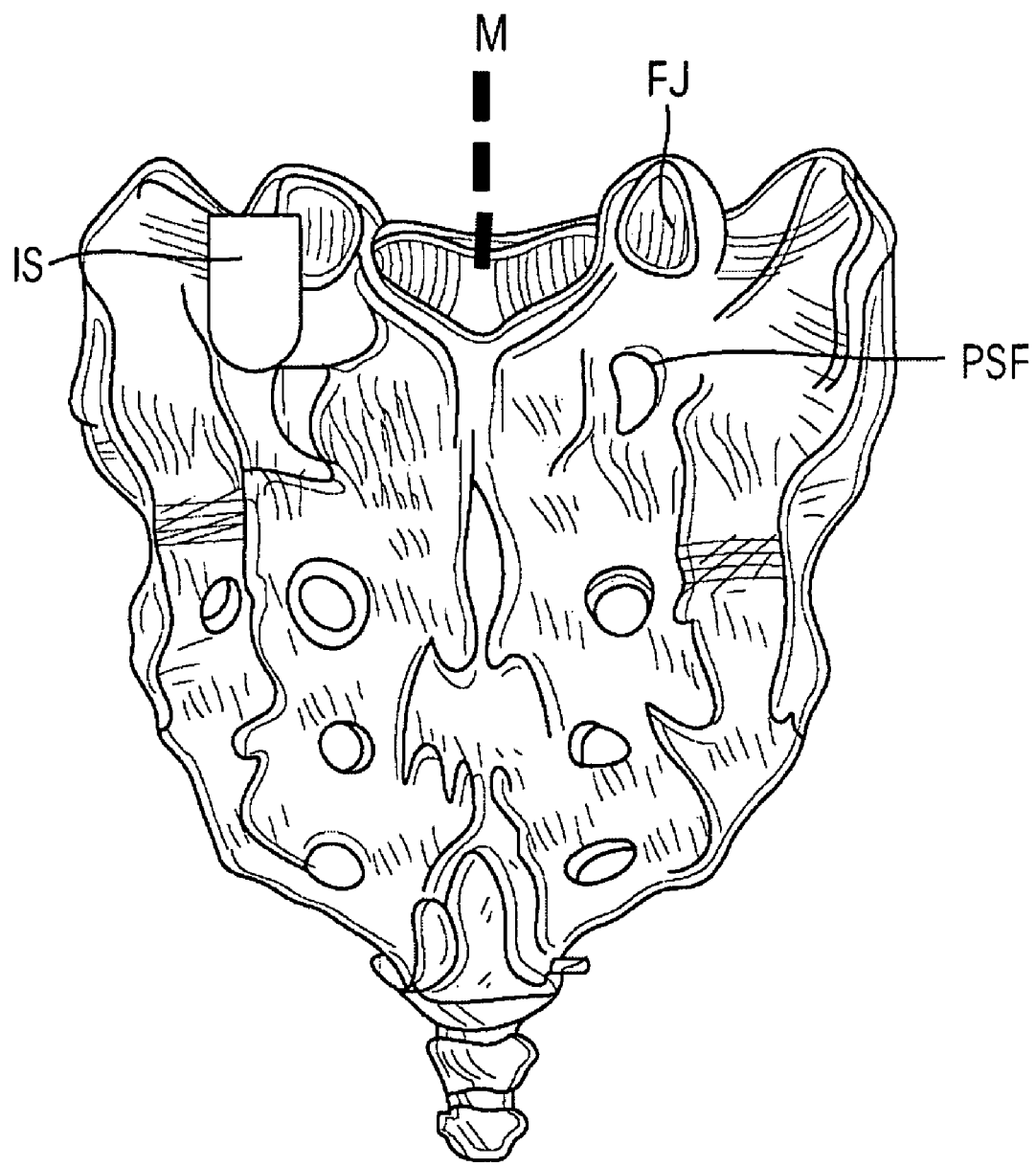
FIG. 3 shows a posterior view of the sacral vertebra with the site of implant insertion.

FIGS. 1A and 1B show perspective views of the first embodiment of the present device. In the illustration, a bone screw has been placed through the left L5 pedicle into the L5 vertebral body. A curvilinear implant 105 is shown crossing the sacrum and entering the L5/S1 disc space 110. An interconnecting rod 115 is used to connect the L5 to S1 fastener. FIG. 2 illustrates the approximate path of the implant while FIG. 3 shows a posterior view of the sacrum. The implant insertion site IS is located between the superior aspect of the posterior sacral surface and the superior aspect of the first posterior sacral foramen PSF and can overlap the L5/S1 facet joint FJ. FIG. 3 shows the approximate insertion site IS and is intended to be illustrative and it should be appreciated that the actual insertion site can vary at least in part from the illustration. Preferably, another pathway is formed through a similar insertion site on the opposite side of the vertebral midline M and an implant is positioned on each side of the midline M.

Figure 4:
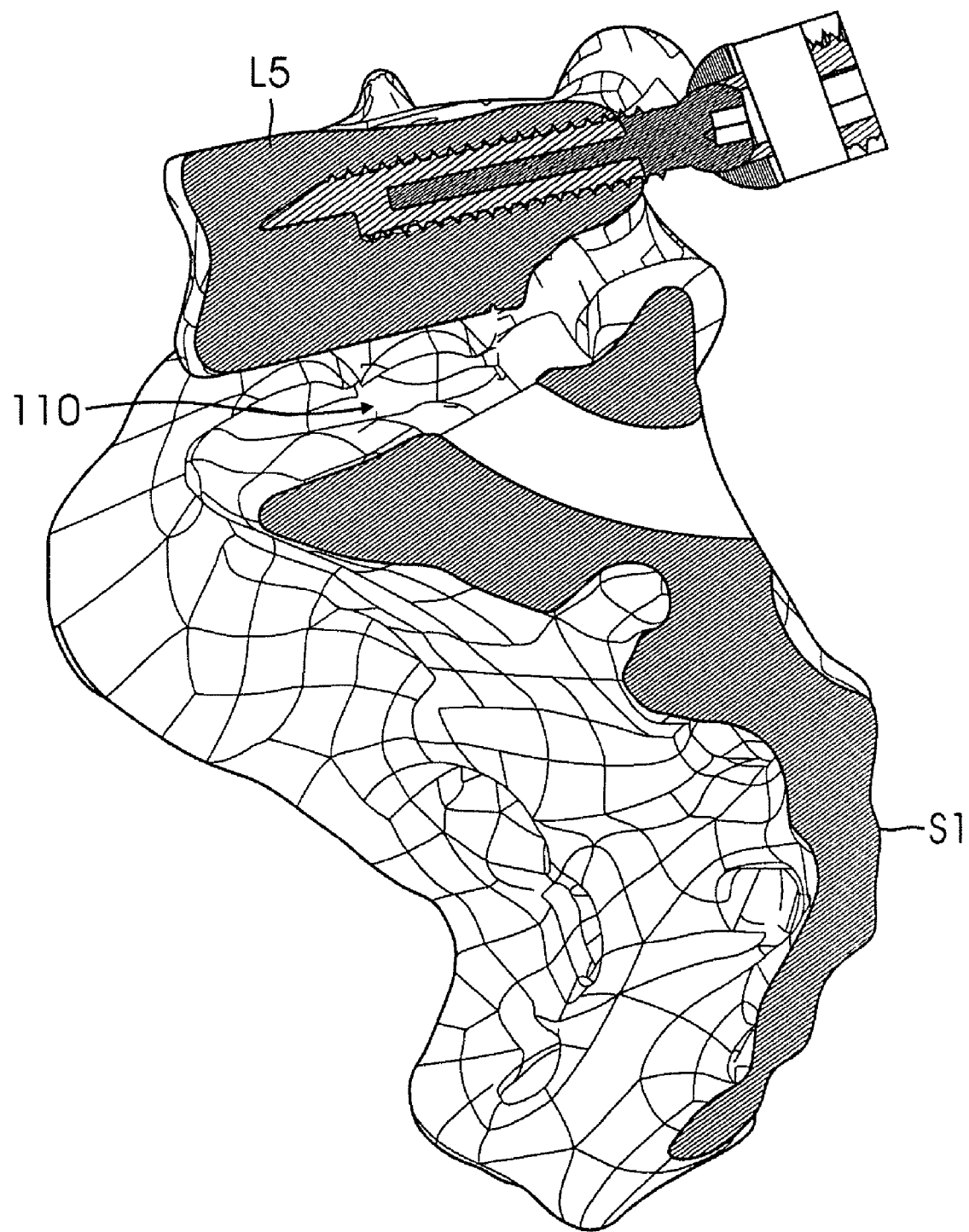
FIG. 4 shows a cross-sectional view of the sacrum and the L5 vertebral body. A pedicle bone screw is shown positioned into the L5 vertebral body. The curvilinear path that will be occupied by the fusion cage is shown in the S1 vertebral body.

The implant 105 is inserted into a pathway or is used to form a pathway through the aforementioned insertion site such that the pathway at least one sacral pedicle, a portion of the first sacral body and enters the L5/S1 disc space The pathway is preferably curvilinear—as shown in FIG. 4—and can be of uniform or non-uniform curvature. Alternatively, the pathway can be linear or substantially linear. The latter is particularly useful when an anterior spondylolisthesis (anterior displacement of the upper vertebra relative to the lower vertebra) of the L5 vertebral body is present relative to the sacrum.

Figure 5:
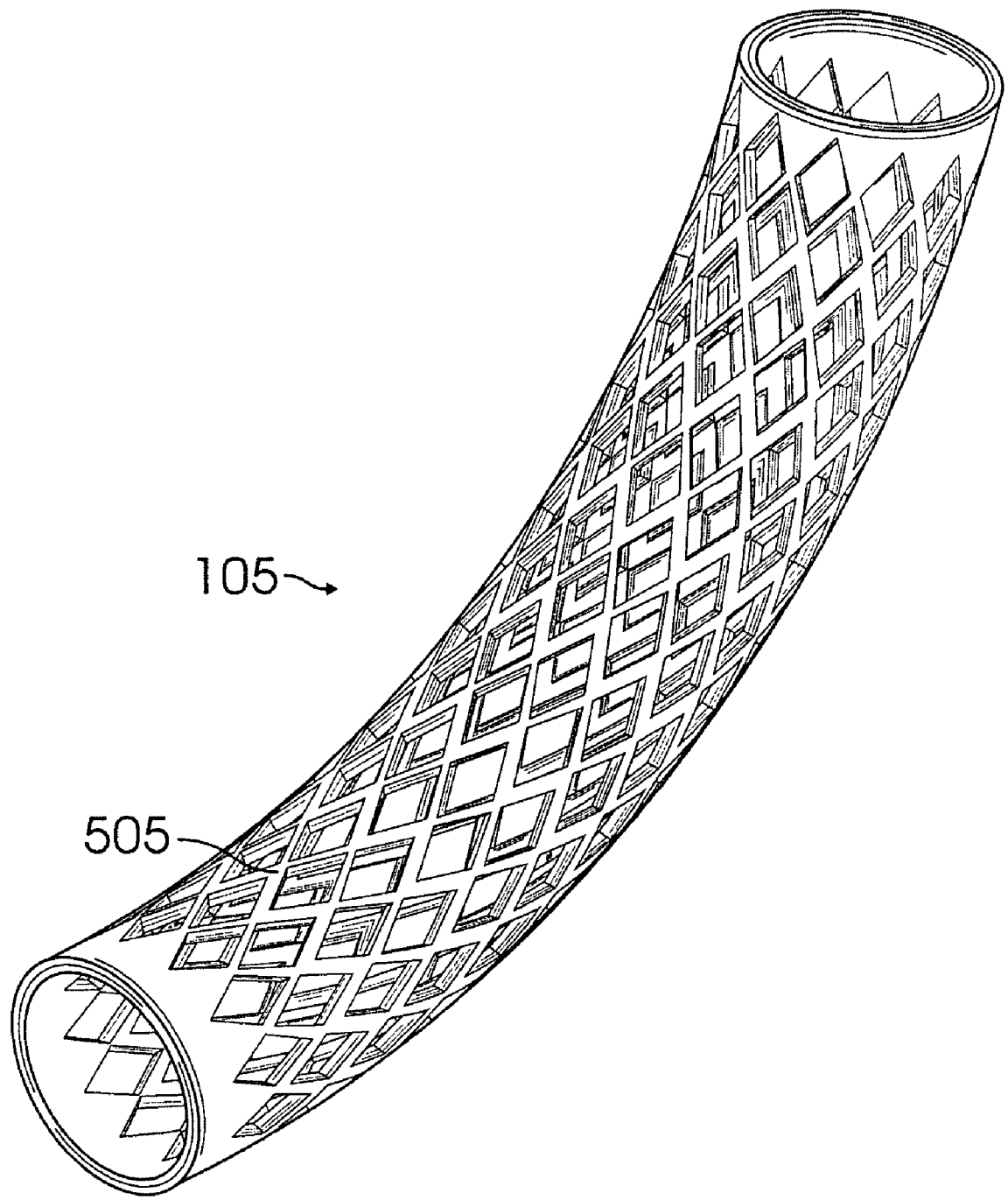
FIG. 5 shows one device embodiment.

The implant 105 can have a variety of structures. For example, the device can consist of a hollow cage having a shape that is adapted to transverse, at a minimum, the aforementioned sacral entry point, the sacral pedicle, the sacral body and then enter the disc space at the L5/S1 level. FIG. 5 illustrates one device embodiment. The implant 105 is a hollow cage with an inner passageway or space that accommodates a bone graft. The side walls 505 of the implant 105 are preferably perforated so as to permit contact and interaction between the contained bone graft and the vertebral bone. While not illustrated, the implant 105 can also include various structural features that serve to enhance anchorage into adjacent bone. For example, the implant 105 can include one or more ridges, indentations, textures, or other structural features (or combinations thereof) within and/or on the implant surfaces that would anchor the implant into the vertebral bone. Any implant member disclosed herein also can be made with a porous ingrowth surface (such as titanium wire mesh, plasma-sprayed titanium, tantalum, porous CoCr, and the like), provided with a bioactive coating, and/or made using tantalum in order to promote bone in-growth or establish a mineralized connection between the bone and the implant. Further, the implant 105 can be at least in part manufactured from carbon nanotubes. In another embodiment, the implant can be substantially or completely comprised of a bone fragment, such as a rib or other bone segment, from the subject undergoing the procedure or from a bone or tissue bank.

Figure 6A:
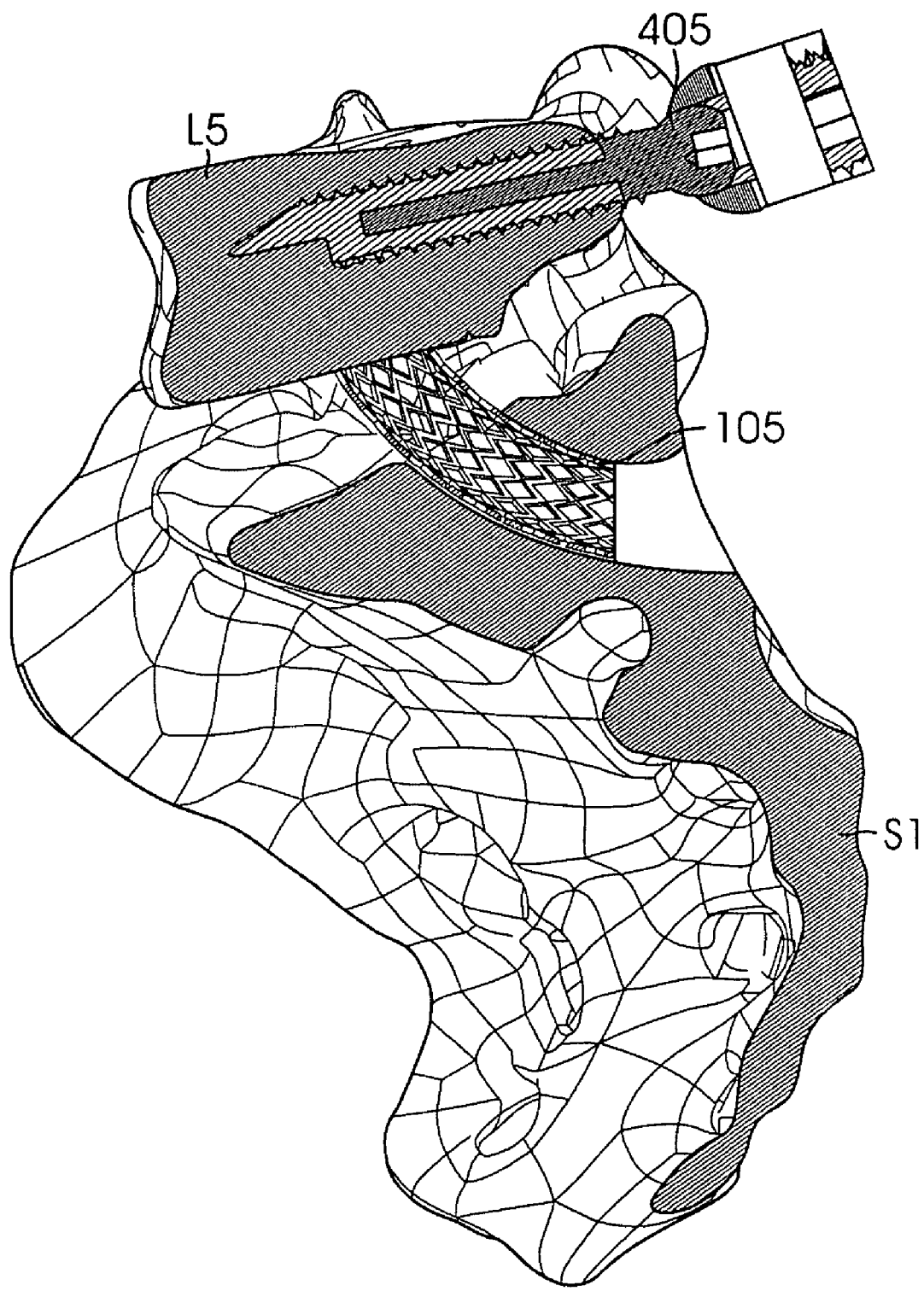
FIG. 6A shows a fusion cage that is implanted within the curvilinear path of the S1 vertebral body. The cage extends onto the inferior surface of the L5 vertebral body. That is, it abuts the inferior L5 surface but does not penetrate it.
Figure 6B:
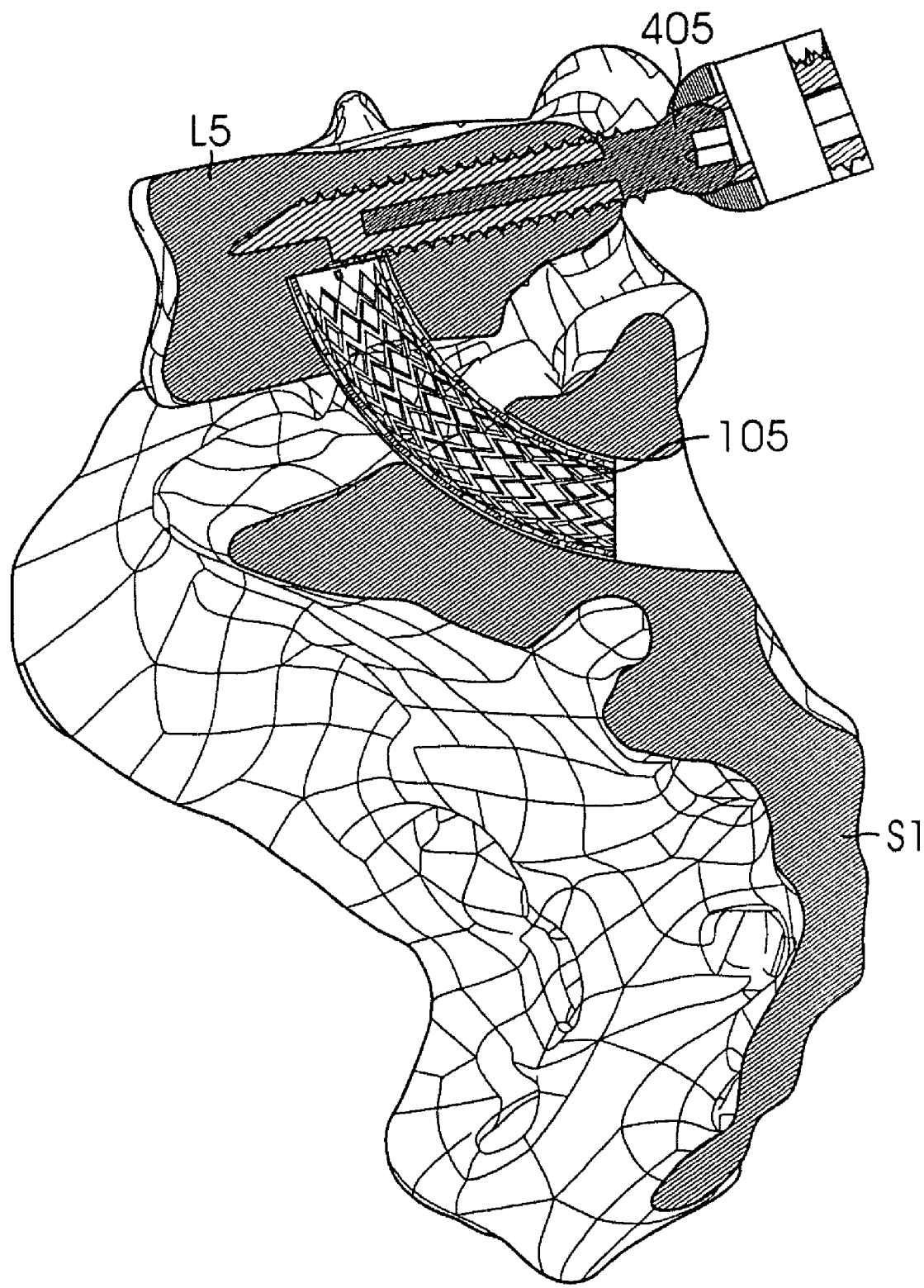
FIG. 6B shows the fusion cage extending into the L5 vertebral body. That is, the cage penetrates the inferior L5 surface.
Figure 7:
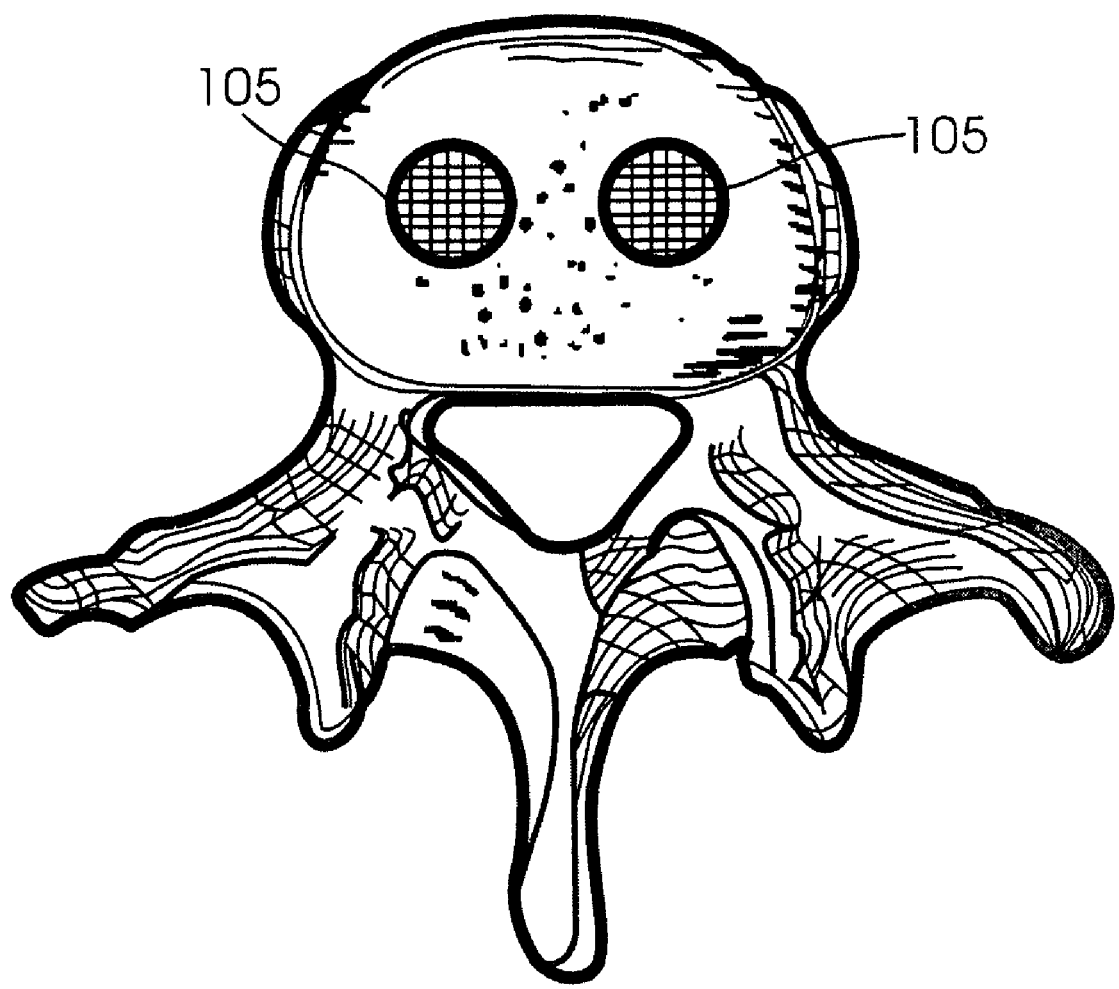
FIG. 7 shows an axial (horizontal plane) view of the L5 vertebral body. When the implant transverses the L5 body, the position of each implant within the L5 body is approximated by the illustration.

FIG. 6A shows an embodiment where the implant 105 rests against the inferior surface of the L5 vertebral body. In another embodiment, the implant 105 penetrates the inferior L5 surface and enters L5 vertebral body (FIG. 6B). The implant can rest against the L5 bone screw 405, as illustrated, or it can rest at any other point within the L5 vertebral body. FIG. 7 shows a view of the L5 vertebra in the horizontal (axial) plane and an approximate position of each implant is shown. It should be appreciated that the implants 105 extend through the L5 vertebral body at a trajectory that is non-perpendicular to the horizontal plane. Thus, the exact implant position in the horizontal plane will vary and the implant position will depend upon the level of the horizontal section selected (within the longitudinal plane).

Figure 8:
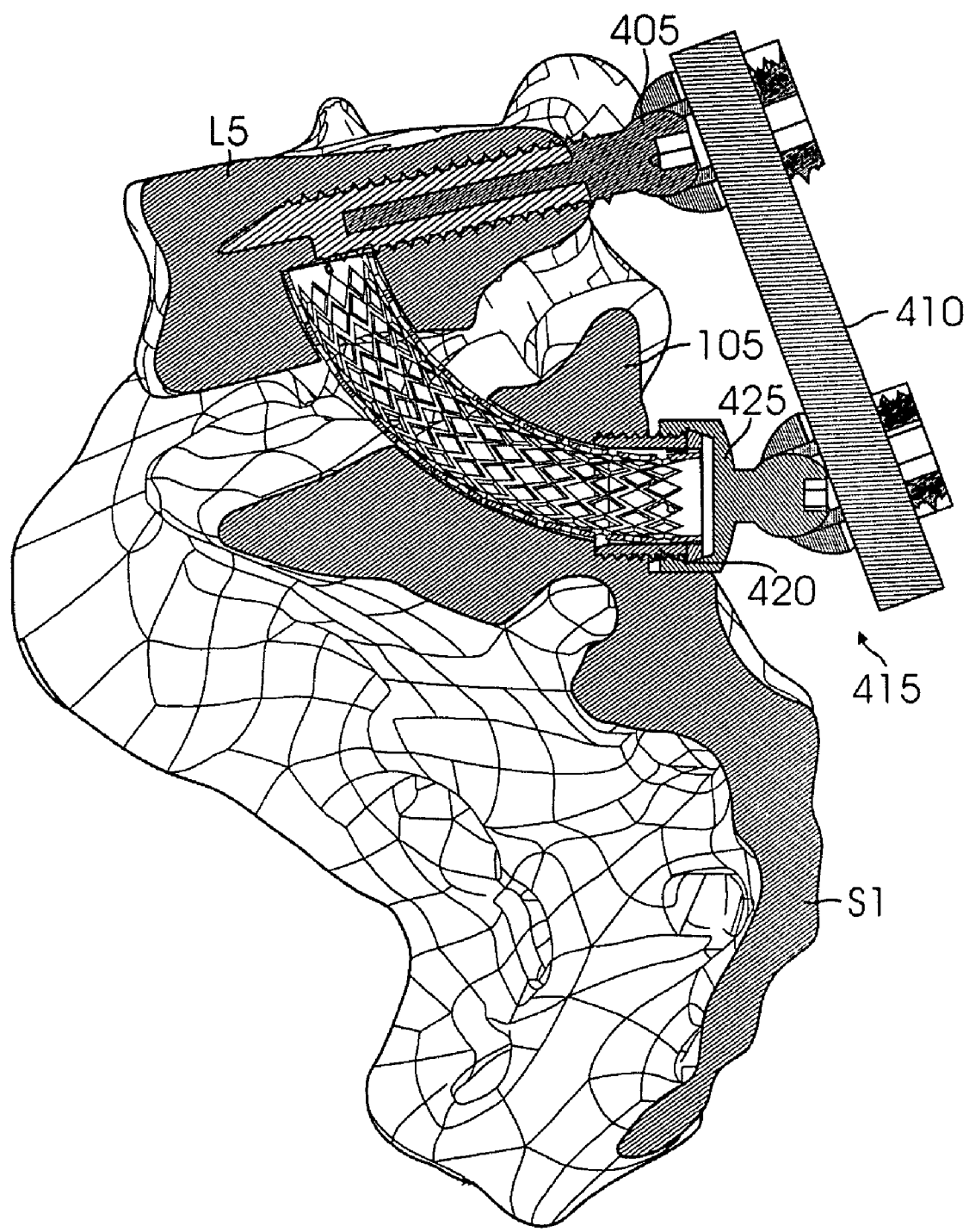
FIG. 8 shows a cross-sectional view of the assembled construct (taken along lines 8-8 of FIG. 1A) used to fuse and immobilize L5 and S1 vertebral bodies.

FIG. 8 shows a cross sectional view of the assembled construct taken along line 8-8 of FIG. 1A. A pedicle bone screw 405 is anchored into the L5 vertebral body, a coupler or sacral attachment 415 (also referred to as a sacral fastener) is anchored into the sacral bone S1 at or near the implant insertion site, and an inter-connecting member 410 (such as an elongated rod) is used to rigidly affix the component members. In assembly, implant 105 can be attached to the sacral attachment 415, as illustrated, or it can alternatively reside unattached within the sacral vertebra S1.

The pathway for implant 105 placement can be formed in various ways. In one embodiment, a bone awl, drill or similar bone carving device of appropriate curvature is positioned at the sacral insertion site and used to forcefully form, such as by drilling or carving, the pathway through the sacral pedicle, sacral body and into the L5/S1 disc space (and possibly beyond). The implant 105 is guided into the carved pathway and the bone graft can be packed into the implant 105 before or after implantation. In another embodiment, a bone awl of curvature substantially similar to that of the implant (but of lesser diameter) is placed within the inner cavity of the implant. The tip of the awl extends beyond the end of the implant. The awl is forcefully guided through the bone so as to form the required pathway and place the implant in a single step. Alternatively, an awl-like tip can be incorporated directly onto the end of the implant.

In another embodiment, a pedicle bone screw 405 is placed into the L5 vertebral body and a guide is attached onto the screw head. The guide rotates in a curvilinear path until it rests immediately posterior to the sacral insertion site. Using the guide, a bone awl, drill or similar bone carving device of appropriate curvature is appropriately positioned by the guide at the sacral insertion site and used to forcefully form, such as by pushing, drilling or carving, the pathway through the sacral pedicle, sacral body and into the L5/S1 disc space (and possibly beyond). The implant 105 is then placed into the carved pathway and, as mentioned, the implant 105 can be filled with bone graft prior to or after implantation.

The sacral attachment 415 is then advanced into the sacrum S1 and attached onto one end of the implant 105. Alternatively, the sacral attachment 415 can be anchored into the sacrum S1 first and the implant 105 passed through a central bore within the sacral attachment 415.

Figures 9A, 9B:
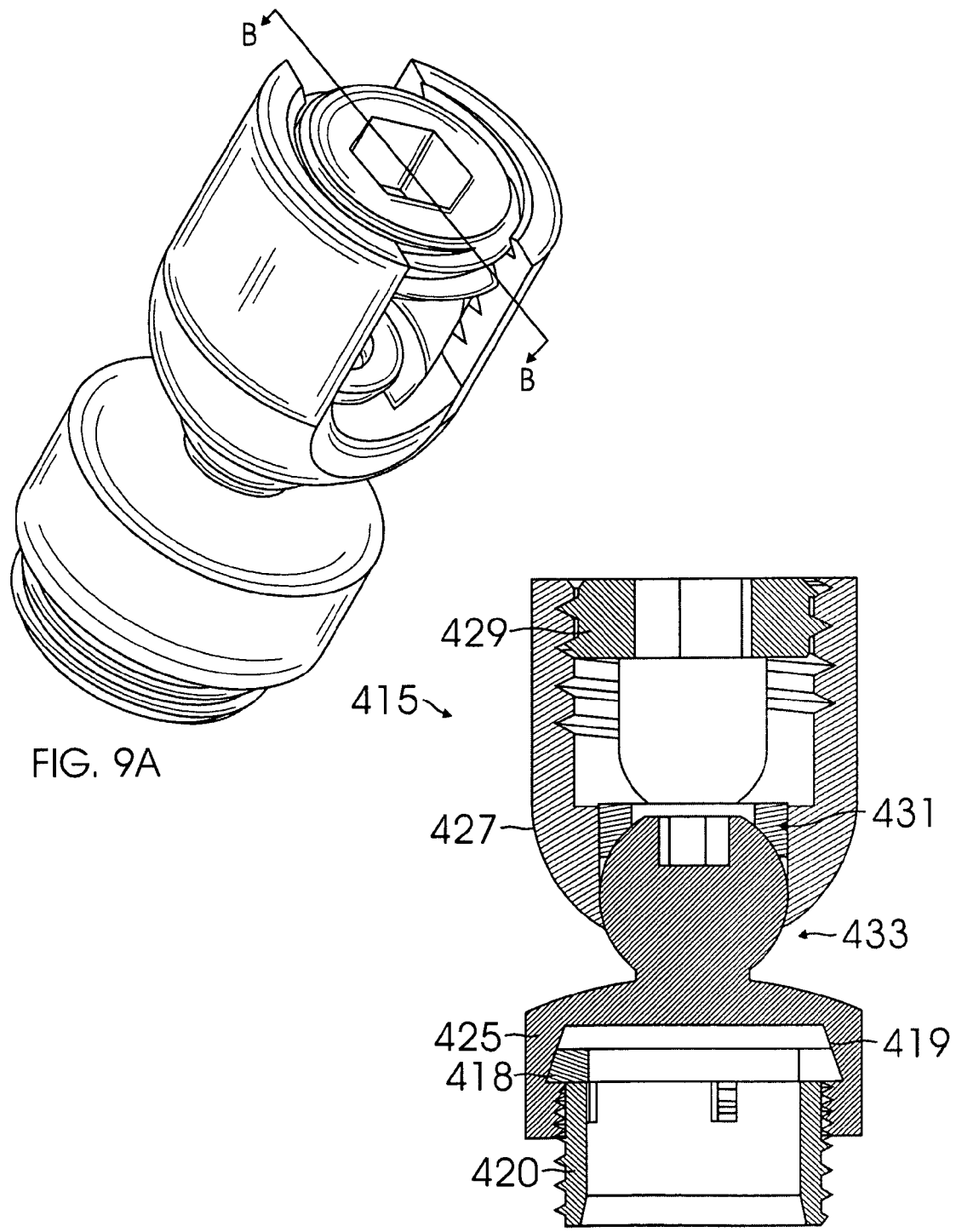
FIG. 9A shows an assembled sacral attachment.
FIG. 9B shows a cross-sectional view of the assembled sacral attachment taken along line B-B of FIG. 9A.
Figure 10:
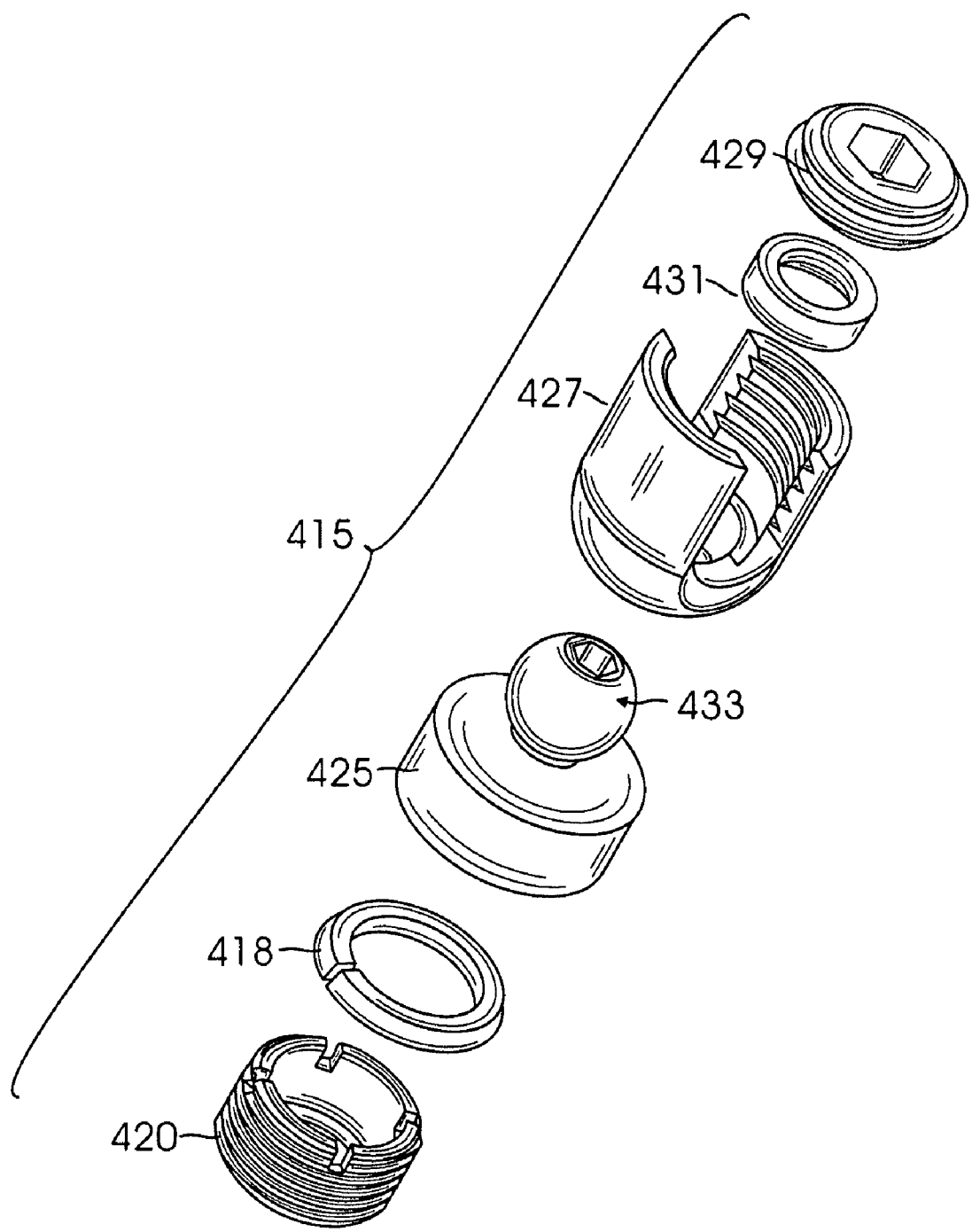
FIG. 10 shows an exploded view of the sacral attachment.

Bone screw 405 preferably has a multi-axial rod receiving member 427 that can be rigidly affixed onto the spherical head 433 of the bone screw and an inter-connecting rod member 410. Multiple embodiments of this device are known in the art and can be used in this application. Alternatively, any adaptable bone screw can be used. Views of the assembled sacral attachment are shown in FIGS. 9A and 9B and the component members of the disassembled device are illustrated in FIG. 10. The sacral attachment 415 includes a first portion 420 with outer threads that anchor into the sacral vertebra. A second portion 425 couples to the outer threads of the first portion 420 and can be tightened onto the first portion and the implant 105 to thereby fixedly couple to the implant 105. Locking ring 418 rests within the inner aspect of member 425. As member 425 is rotated and advanced onto the threads of member 420, the locking ring 418 is forced along angled inner wall 419 of member 425. In this way, the locking ring 418 is forcefully tightened onto the tip of implant 105 and the implant 105 is rigidly affixed to the sacral attachment 415. The sacral attachment 415 includes poly-axial rod receiving member 427 that can receive an inter-connecting rod member 410 (not shown in the FIGS. 9-10). With rod 410 appropriately positioned within receiving member 427, locking nut 429 is rotatably advanced onto the rod member 410. Locking nut 429 applies force to the rod which transmits force to cap member 431 and immobilizes the rod 410 and receiving member 427 relative to spherical head 433 of the sacral attachment 415.

When the locking nut 429 is appropriately tightened within bone screw 405 and sacral attachment 415, the construct members are rigidly affixed to one another. While the procedure can be preformed on one side, it is preferably performed on each side of the midline so as to provide complete bilateral fixation of both the anterior and posterior aspect of the sacrum and L5 vertebral body.

Figure 12A:
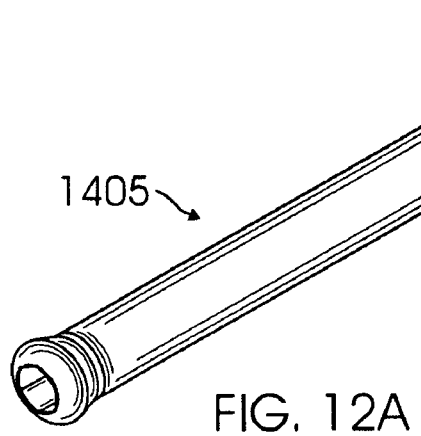
FIGS. 12A, B and C show perspective, side and top views, respectively, of a bone screw.
Figure 12B:
Figure 12C:
Figure 13:
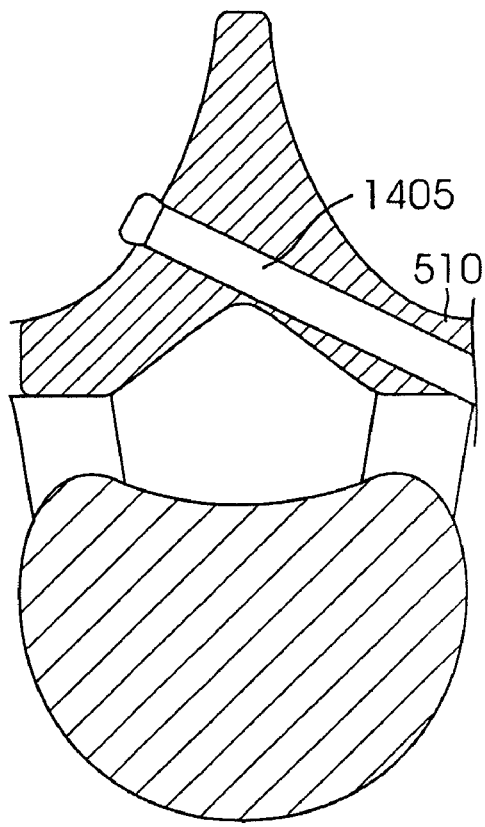
FIG. 13 shows a bone screw transversing the central aspect of the contra-lateral lamina.
Figure 14:
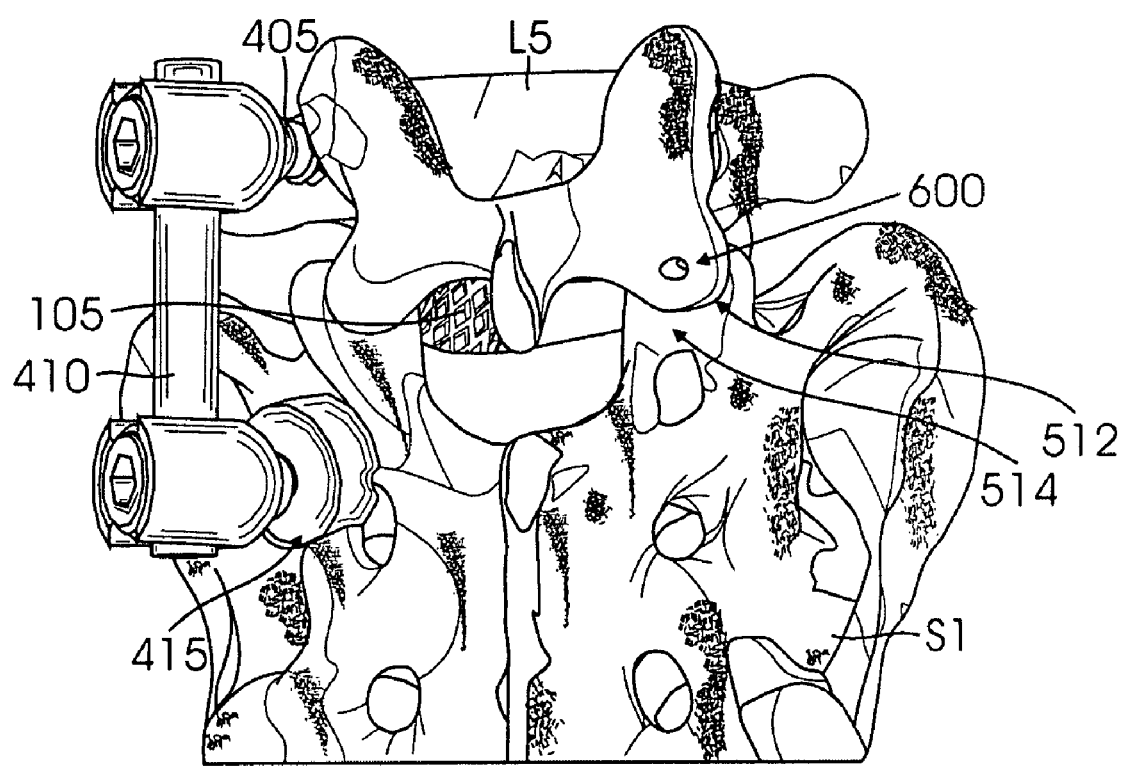
FIG. 14 shows another embodiment of a device for the fixation of the contra-lateral L5/S1 facet joint.

Devices and methods for the complete segmental fixation through a unilateral approach are shown in FIGS. 11 through 13. A curvilinear cage 105 is placed through the pedicle portion of the first sacral vertebra S1 across the L5/S1 space and into the L5 vertebral body as previously described. An L5 screw 405 and the sacral attachment 415 are connected by the interconnecting rod 410. The L5/S1 facet joint on the contra-lateral site of the vertebral midline is then affixed and immobilized using a bone screw 1405 that is inserted into the L5 lamina from the same side as the implant 105 (FIGS. 11A and 11B). FIGS. 12A, B, and C show perspective, side and top views of the bone screw 1405. The screw has a head that is adapted to accept a complimentary screw driver and a long, partially threaded shaft. After insertion on the same side of the vertebral midline as the implant 105, bone screw 1405 transverses the central aspect of the contra-lateral lamina 510 as shown in FIG. 13. The screw trajectory guides the tip across the contra-lateral L5/S1 facet joint 512 (shown in FIG. 14) and into the contra-lateral superior S1 facet surface 514 (shown in FIG. 14). In this way, the contra-lateral facet joint 512 is also immobilized. Alternatively, screw 1405 can be made entirely of bone or have a central cavity for insertion of a bone graft (similar to a cage). Lastly, the screw 1405 can have a synthetic inner core and have on outer bone covering.
T FIG. 14 illustrates an alternative device for the fixation of the contra-lateral L5/S1 facet joint 512 after ipsi-lateral L5 to S1 fusion using implant 105. The contra-lateral L5/S1 facet joint 512 is accessed (preferably using percutaneous technique) and a screw 600 is threaded into the facet joint 512 as illustrated. Screw 600 can have a central cavity for insertion of a bone graft (similar to a cage) or it can be made entirely of bone. Alternatively, screw 600 can have a synthetic inner core and have on outer bone covering. Lastly, a larger screw can be used to enter the inferior facet of the L5, transverse the L5/S1 facet joint 512 and extend to the S1 facet joint or to the underlying S1 pedicle (not shown).

Figure 15B:
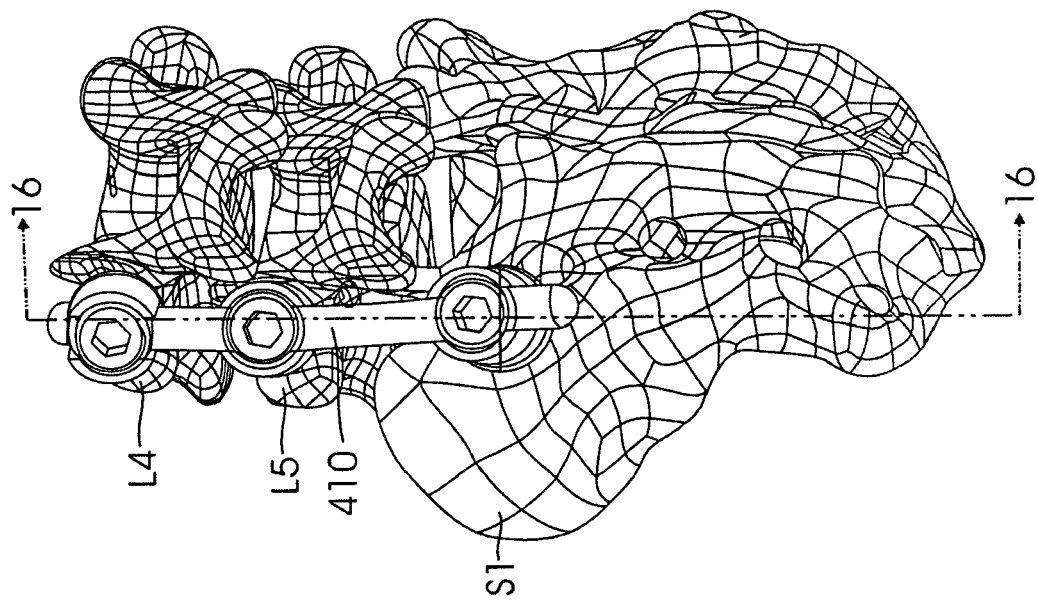
FIGS. 15A and 15B show a construct used to fuse and immobilize L4, L5 and S1 vertebral bodies.
Figure 15A:
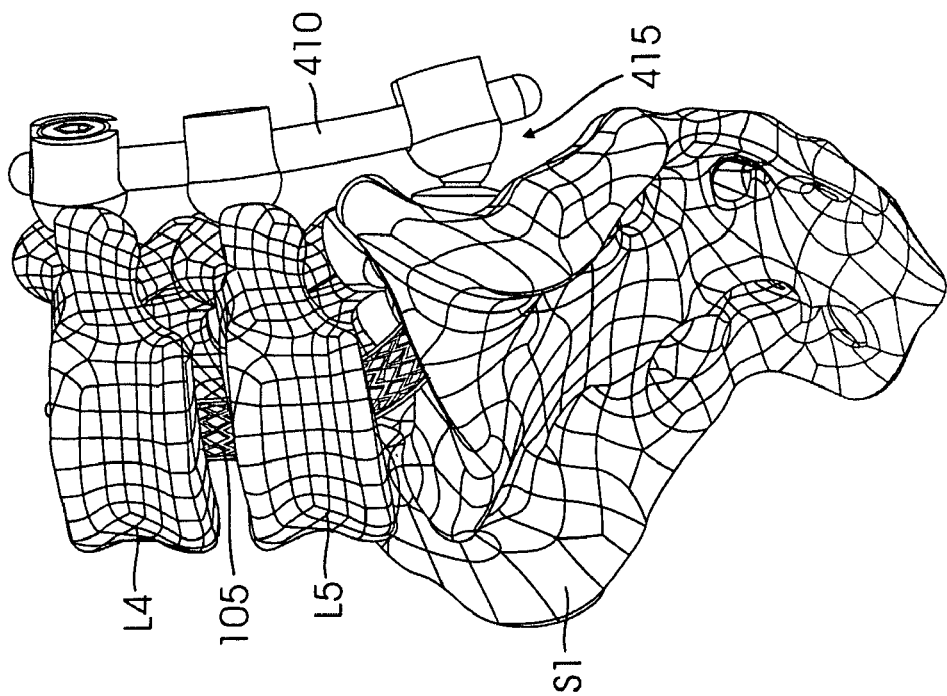
Figure 16:
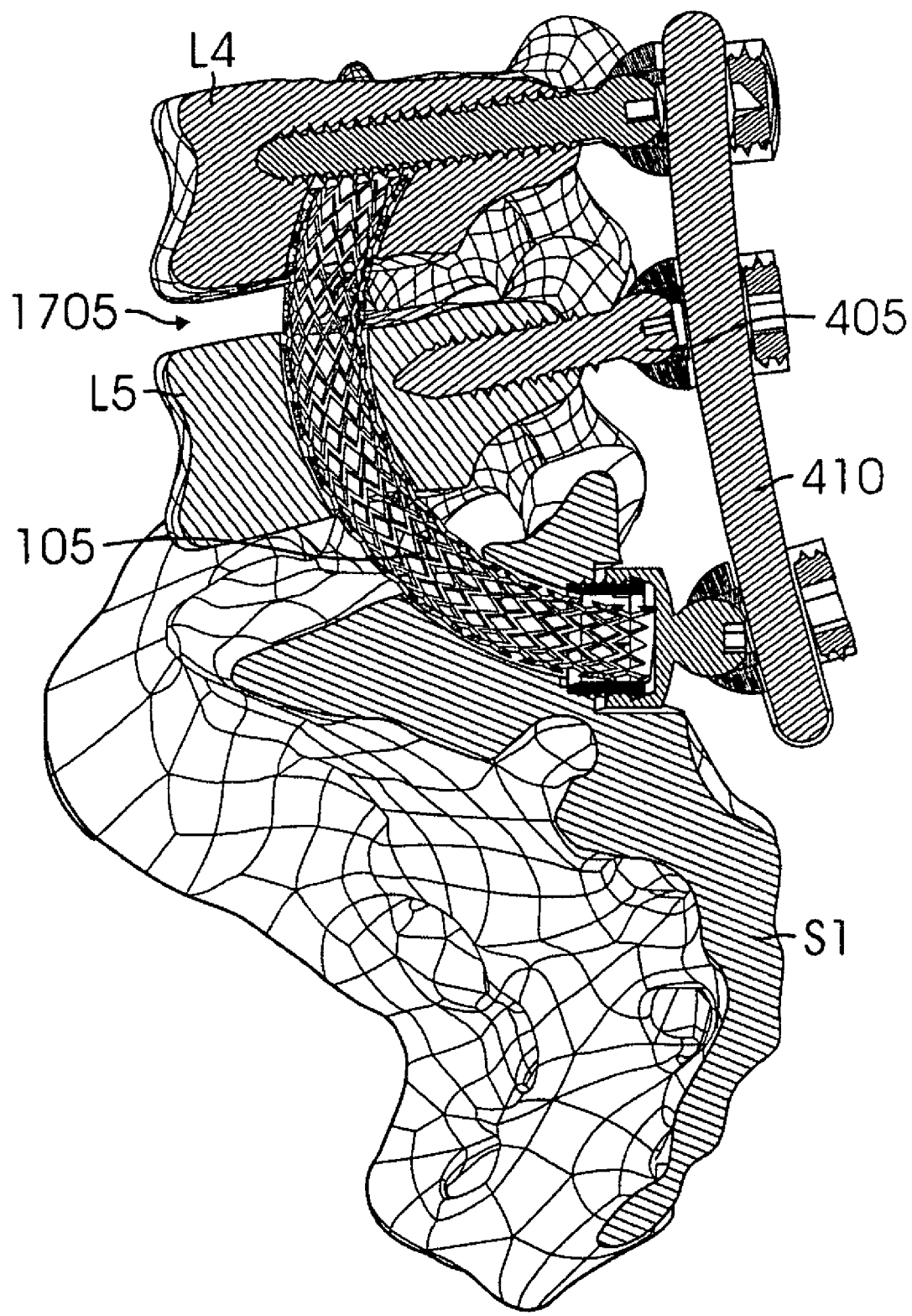
FIG. 16 shows a cross-sectional view of the construct taken along line A-A of FIG. 15B.

In FIGS. 15 and 16, fusion of the L4 to S1 vertebral bodies is illustrated. A bone screw 405 is placed into the L5 pedicle and a guide is used to produce the pathway through the sacrum, L5/S1 disc space and L5 vertebral body. A relatively short L5 screw 405 is used such that the implant 105 can be pushed through the L5 body without contacting screw 405. The implant 105 crosses the L4/5 disc space 1705 and comes to rest at the inferior surface of the L4 vertebral body or the implant 105 can be passed into the L4 vertebra. The implant 105 can be filled with bone graft and then placed into the carved bony defect or filled with graft material after insertion. A connection rod 410 can be used to connect the vertebral screws and provide additional fixation. The rod 410 can extend from L5 to the sacrum or an additional screw can be placed into the L4 vertebra and the rod can extend from the L4 vertebra to the sacrum S1. This method provides fusion of the L4 vertebral body, L5 vertebral body and the sacrum. The numerous variations described above for the L5 to sacral fusion are equally applicable here and are considered additional embodiments. One such embodiment permits unilateral fixation of L4 to S1 by immobilization of the contra-lateral L4/5 and L5/S1 facet joints using facet screws that are inserted into the L4 and L5 laminas, respectively, from the same side as implant 105. Use of this method in L5 to sacral fusion is illustrated in FIGS. 11 to 13 and, for brevity, will not be repeated.

Figure 17B:
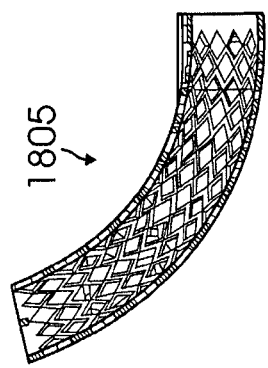
FIGS. 17A and 17B show a device and method of vertebral distraction. A first conduit is placed through the sacral pedicle and into the L5/S1 disc space—as shown in FIG. 17A. A second conduit of smaller diameter is shown in FIG. 17B.
Figure 17A:
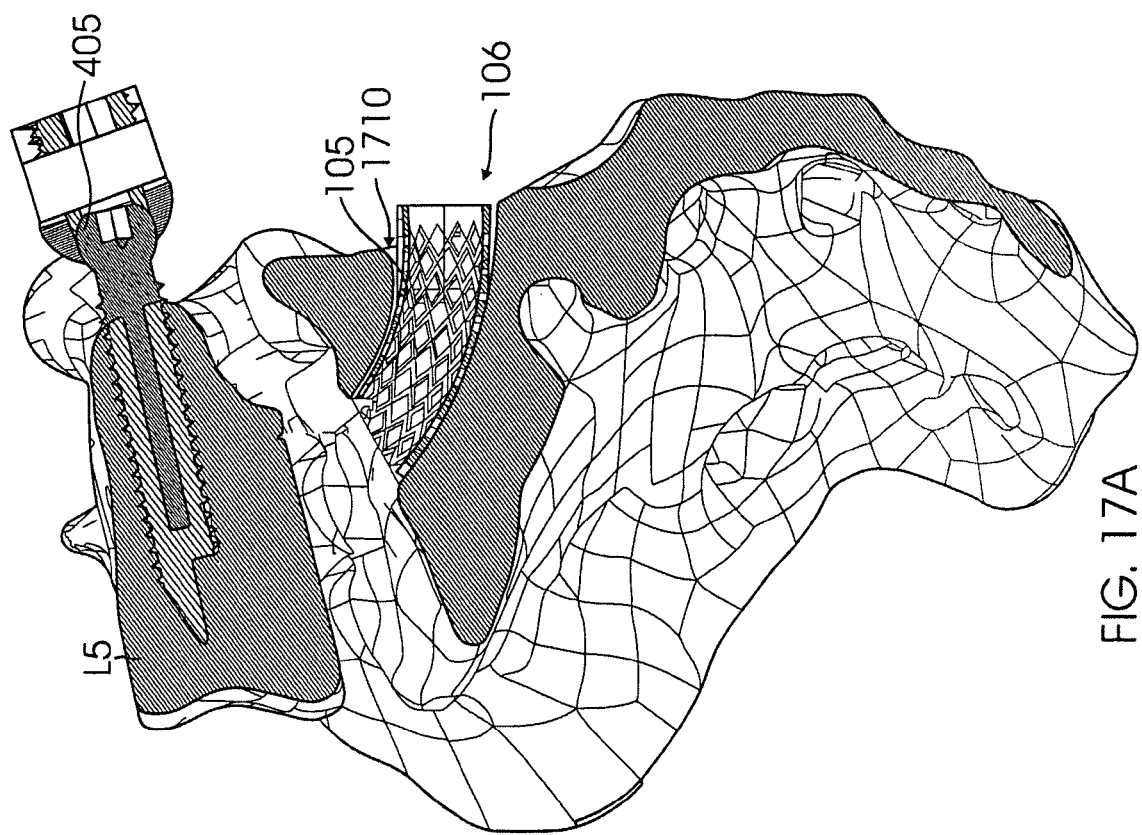
Figure 18:
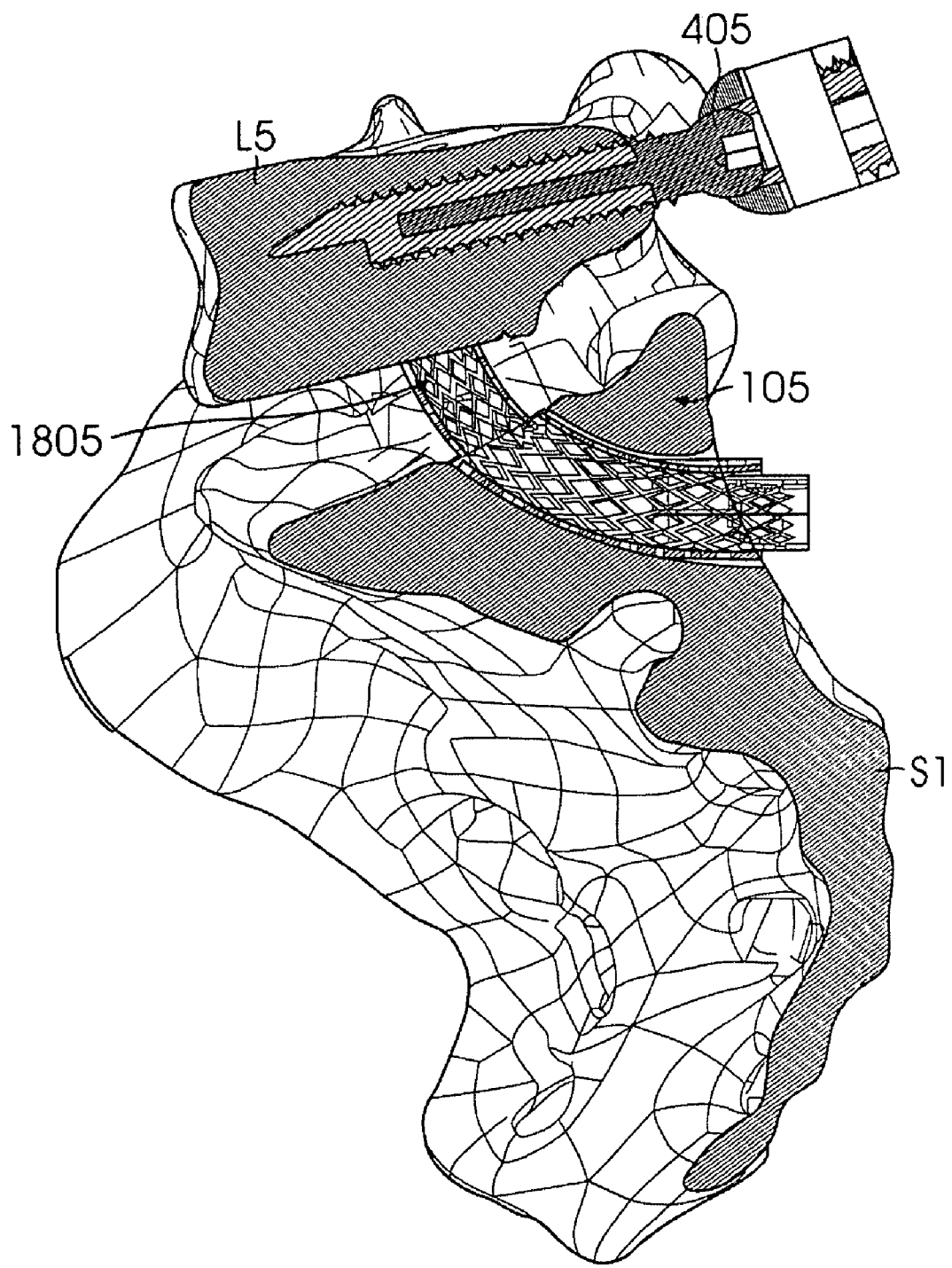
FIG. 18 shows a second, smaller conduit inserted through the larger, first conduit. The distal end of the second conduit extends onto or into the inferior surface of the L5 vertebral body. Movement of the first and second conduits will cause the attached vertebral bodies to move relative to one another.

FIGS. 17 and 18 illustrate an implant and method for vertebral distraction. A pathway of appropriate curvature is formed through the sacral entry point 1710, at least one sacral pedicle, the first sacral body and into the L5/S1 disc space. First implant member 105 with central bore 106 is placed into the carved pathway so as to form a tight fit between implant and pathway—as shown in FIG. 17A. A second implant member 1805 has a similar curvature and smaller diameter than first implant member 105. The second implant member 1805 is illustrated in FIG. 17B and is sized and shaped to be inserted into central bore 106 of implant member 105. FIG. 18 shows second implant member 1805 positioned within first implant member 105 where the distal end of the implant member 1805 extends beyond the distal end of member 105 and abuts the inferior surface of the L5 vertebral body. With the implant member 1805 so positioned and with implant member 105 held stationary, a force is applied to member 1805 so as to move it towards the L5 vertebral body and thereby distract the L5 vertebral body away from the sacrum.

As an alternative method of vertebral distraction, a pathway of appropriate curvature is formed as described above. An implant member 105 is placed into the formed pathway so that it abuts or attaches to the inferior surface of the L5 vertebral body (such as seen in FIG. 6A). A sacral attachment 415 is attached onto the sacrum (such as seen in FIG. 8). When force is applied to the implant member 105 transversing the pathway, the implant member 105 and sacral attachment 415 undergo relative distraction and produce comparable movement in the attached L5 vertebra and sacrum.

The disclosed devices or any of their components can be made of any biologically adaptable or compatible materials. Numerous materials are currently considered acceptable for biological implantation. They can include, but are not limited to, stainless steel, titanium, tantalum, combination metallic alloys, various plastics, resins, ceramics, biologically absorbable materials and the like. Any components can be also coated/made with osteo-conductive (such as demineralized bone matrix, hydroxyapatite, and the like) and/or osteo-inductive (such as Transforming Growth Factor "TGF-B," Platelet-Derived Growth Factor "PDGF," Bone-Morphogenic Protein "BMP," and the like) bio-active materials that promote bone formation. Further, any surface can be made with a porous ingrowth surface (such as titanium wire mesh, plasma-sprayed titanium, tantalum, porous CoCr, and the like), provided with a bioactive coating, made using tantalum, and/or helical rosette carbon nanotubes (or other carbon nanotube-based coating) in order to promote bone in-growth or establish a mineralized connection between the bone and the implant, and reduce the likelihood of implant loosening. The system or any of its components can also be entirely or partially made of a shape memory material or other deformable material.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:
1. A method for placement of an orthopedic implant between a sacrum of a vertebral column and a vertebral bone that is immediately superior to the sacrum, comprising:
    penetrating a posterior bone surface of the sacrum at an area of bone surface penetration that is bounded superiorly by at least a portion of a sacral facet joint, and bounded inferiorly by at least a portion of a first posterior sacral foramen;

forming a first pathway from the area of bone penetration on the posterior surface of the sacrum, through at least one sacral pedicle, and through at least a segment of a first sacral vertebral body;

advancing the first pathway through at least a segment of a disc space that is immediately superior to the sacrum, wherein the pathway further extends to abut at least a segment of an inferior surface of the vertebral bone that is immediately superior to the sacrum;

advancing the orthopedic implant through the area of bone penetration on the posterior surface of the sacrum, wherein the implant extends along a first axis from a proximal end to a distal end, and wherein at least a segment of the implant extends along the first axis in a non-linear trajectory;

positioning the orthopedic implant at least partially within the first pathway, wherein at least a segment of the implant and bone forming material rests within the disc space that is immediately superior to the sacrum.

2. A method as in claim 1, wherein the implant is used to penetrate the posterior surface of the sacrum and to form at least a portion of the first pathway.

3. A method as in claim 1, wherein a separate instrument is used to form the first pathway prior to advancing the implant into the sacrum.

4. A method as in claim 1, wherein the pathway penetrates a surface of the vertebral bone that is immediately superior to the sacrum.

5. A method as in claim 1, wherein at least a segment of the implant is positioned within the vertebral bone that is immediately superior to the sacrum.

6. A method as in claim 1, wherein the implant extends along the first axis in a non-linear trajectory of uniform curvature.

7. A method as in claim 1, wherein the implant extends along the first axis in a non-linear trajectory of non-uniform curvature.

8. A method as in claim 1, wherein a sacral fastener is advanced into the sacrum and positioned to abut the implant.

9. A method as in claim 1, wherein the procedure is minimally invasive.

10. A method as in claim 1, wherein the procedure is performed in a percutaneous manner.

11. A method as in claim 1, wherein a bone forming material is advanced through the area of bone penetration on the posterior surface of the sacrum and at least partially into the disc space that is immediately superior to the sacrum.

12. A method as in claim 1, wherein the implant contains an internal cavity adapted to house a bone forming material.

13. A method as in claim 1, wherein the first pathway extends along a first side of the sacral midline, wherein the facet joint formed by the interaction of the sacrum and the immediately superior vertebral bone is immobilized by a first fastener, wherein the immobilized facet joint is on the opposite side of the sacral midline from the first pathway.

14. A method for placement of an orthopedic implant between a sacrum Segment of a vertebral column and a vertebral bone that is immediately superior to the sacrum, comprising:

penetrating a posterior bone surface of the sacrum at an area of bone surface penetration that is bounded superiorly by at least a portion of a sacral facet joint, and bounded inferiorly by at least a portion of a first posterior sacral foramen, forming a first pathway that extends along a first axis from the area of bone penetration on the posterior surface of the sacrum, through at least one sacral pedicle, through at least a segment of a first sacral vertebral body, wherein at least a segment of the first pathway extends along the first axis in a non-linear trajectory;

advancing the first pathway through at least a segment of the disc space that is immediately superior to the sacrum, wherein the pathway further extends to abut at least a segment of an inferior surface of the vertebral bone that is immediately superior to the sacrum;

advancing the orthopedic implant through the area of bone penetration on the posterior surface of the sacrum, wherein the implant is at least partially positioned within the first pathway, and wherein at least a segment of the implant is positioned within the disc space that is immediately superior to the sacrum.

15. A method as in claim 14, wherein the implant is used to penetrate the posterior surface of the sacrum and to form at least a portion of the first pathway.

16. A method as in claim 14, wherein a separate instrument is used to form the first pathway prior to advancing the implant into the sacrum.

17. A method as in claim 14, wherein the pathway penetrates a surface of the vertebral bone that is immediately superior to the sacrum.

18. A method as in claim 14, wherein at least a segment of the implant is positioned within the vertebral bone that is immediately superior to the sacrum.

19. A method as in claim 14, wherein the implant extends along the first axis in a non-linear trajectory of uniform curvature.

20. A method as in claim 14, wherein the implant extends along the first axis in a non-linear trajectory of non-uniform curvature.

21. A method as in claim 14, wherein a sacral fastener is advanced into the sacrum and positioned to abut the implant.

22. A method as in claim 14, wherein the procedure is minimally invasive.

23. A method as in claim 14, wherein the procedure is performed in a percutaneous manner.

24. A method as in claim 14, wherein a bone forming material is advanced through the area of bone penetration on the posterior surface of the sacrum and at least partially into the disc space that is immediately superior to the sacrum.

25. A method as in claim 14, wherein the implant contains an internal cavity adapted to house a bone forming material.

26. A method as in claim 14, wherein the first pathway extends along a first side of the sacral midline, wherein the facet joint formed by the interaction of the sacrum and the immediately superior vertebral bone is immobilized by a first fastener, wherein the immobilized facet joint is on the opposite side of the sacral midline from the first pathway.

27. A method used to stabilize movement between a sacrum segment of a vertebral column and a vertebral bone that is immediately superior to the sacrum, comprising:

penetrating a posterior bone surface of the sacrum at an area of bone surface penetration that is bounded superiorly by at least a portion of a sacral facet joint, and bounded inferiorly by at least a portion of a first posterior sacral foramen;

forming a first pathway from the area of bone penetration on the posterior surface of the sacrum, through at least one sacral pedicle, and through at least a segment of the first sacral vertebral body;

advancing the first pathway through at least a segment of the disc space that is immediately superior to the sacrum, wherein the pathway further extends to abut at least a segment of an inferior surface of the vertebral bone that is immediately superior to the sacrum;

advancing an orthopedic implant through the area of bone penetration on the posterior surface of the sacrum and at least partially within the first pathway, wherein at least a segment of the implant is positioned within the disc space that is immediately superior to the sacrum;

driving a first fastener into the sacrum, wherein a least a segment of the fastener is contained within a portion of the first pathway, wherein the first fastener contains at least one housing member adapted to receive an interconnecting rod member, wherein the housing member contains a locking feature that transitions from a first state to a second state, and wherein the housing member is movable relative to the rod member when the locking feature is in the first state and rigidly affixed to the rod member when the locking feature is in the second state;

driving a threaded shank portion of a second fastener into the vertebral bone immediately superior to the sacrum, wherein the second fastener further contains at least one housing member adapted to receive an interconnecting rod member, wherein the housing member contains a locking feature that transitions from a first state to a second state, and wherein the housing is movable relative to the rod member when the locking feature is in the first state and rigidly affixed to the rod member when the locking feature is in the second state;

coupling a first segment of an interconnecting rod member to the housing member of the first fastener and coupling a second segment of the interconnecting member to the housing member of the second fastener;

transitioning the locking feature of each of the first and second fasteners from the first state to the second state.

28. A method as in claim 27, wherein the orthopedic implant positioned within the disc space is adapted to promote a bone fusion across the implanted disc space.

29. A method as in claim 27, wherein the orthopedic implant extends along a first axis from a proximal end to a distal end, and wherein at least a segment of the implant extends along the first axis in a non-linear trajectory.

30. A method as in claim 27, wherein the first pathway extends along a first axis from the area of bone penetration on the posterior surface of the sacrum, and wherein at least a segment of the first pathway extends along the first axis in a non-linear trajectory.

31. A method as in claim 27, wherein the implant is used to penetrate the posterior surface of the sacrum and to form at least a portion of the first pathway.

32. A method as in claim 27, wherein a separate instrument is used to form the first pathway prior to advancing the implant into the sacrum.

33. A method as in claim 27, wherein the pathway penetrates a surface of the vertebral bone that is immediately superior to the sacrum.

34. A method as in claim 27, wherein at least a segment of the implant is positioned within the vertebral bone that is immediately superior to the sacrum.

35. A method as in claim 27, wherein the implant extends along the first axis in a non-linear trajectory of uniform curvature.

36. A method as in claim 27, wherein the implant extends along the first axis in a non-linear trajectory of non-uniform curvature.

37. A method as in claim 27, wherein a sacral fastener is advanced into the sacrum and positioned to abut the implant.

38. A method as in claim 27, wherein the procedure is minimally invasive.

39. A method as in claim 27, wherein the procedure is performed in a percutaneous manner.

40. A method as in claim 27, wherein a bone forming material is advanced through the area of bone penetration on the posterior surface of the sacrum and at least partially into the disc space that is immediately superior to the sacrum.

41. A method as in claim 27, wherein the implant contains an internal cavity adapted to house a bone forming material.

42. A method as in claim 27, wherein the first pathway extends along a first side of the sacral midline, wherein the facet joint formed by the interaction of the sacrum and the immediately superior vertebral bone is immobilized by a first fastener, wherein the immobilized facet joint is on the opposite side of the sacral midline from the first pathway.

43. A method used to stabilize movement between a sacrum segment of a vertebral column and a vertebral bone that is immediately superior to the sacrum, wherein comprising:

penetrating a posterior bone surface of the sacrum at an area of bone surface penetration that is on a first side of the vertebral column midline, bounded superiorly by at least a portion of a sacral facet joint, and bounded inferiorly by at least a portion of a first posterior sacral foramen, forming a first pathway from the area of bone penetration on the posterior surface of the sacrum, through at least one sacral pedicle, and through at least a segment of the first sacral vertebral body;

advancing the first pathway through at least a segment of the disc space that is immediately superior to the sacrum, wherein the pathway further extends to abut at least a segment of an inferior surface of the vertebral bone that is immediately superior to the sacrum;

advancing an orthopedic implant through the area of bone penetration on the posterior surface of the sacrum and at least partially within the first pathway, wherein the implant is advanced ipsilateral to the area of posterior sacrum bone penetration, and wherein at least a segment of the implant is positioned within the disc space that is immediately superior to the sacrum;

advancing a bone fastener along a second pathway, wherein the second pathway starts ipsilateral to the first pathway, crosses the vertebral column midline and penetrates the joint surface of the facet joint between the sacrum and the immediately superior vertebral bone, wherein the penetrated facet is facet is contra-lateral to side of the first pathway, and wherein the fastener prevents movement across the penetrated facet joint.

44. A method as in claim 43, wherein the orthopedic implant positioned within the disc space is adapted to promote a bone fusion across the implanted disc space.

45. A method as in claim 43, wherein the orthopedic implant extends along a first axis from a proximal end to a distal end, and wherein at least a segment of the implant extends along the first axis in a non-linear trajectory.

46. A method as in claim 43, wherein the first pathway extends along a first axis from the area of bone penetration on the posterior surface of the sacrum, and wherein at least a segment of the first pathway extends along the first axis in a non-linear trajectory.

47. A method as in claim 43, wherein the implant is used to penetrate the posterior surface of the sacrum and to form at least a portion of the first pathway.

48. A method as in claim 43, wherein a separate instrument is used to form the first pathway prior to advancing the implant into the sacrum.

49. A method as in claim 43, wherein the pathway penetrates a surface of the vertebral bone that is immediately superior to the sacrum.

50. A method as in claim 43, wherein at least a segment of the implant is positioned within the vertebral bone that is immediately superior to the sacrum.

51. A method as in claim 43, wherein the implant extends along the first axis in a non-linear trajectory of uniform curvature.

52. A method as in claim 43, wherein the implant extends along the first axis in a non-linear trajectory of non-uniform curvature.

53. A method as in claim 43, wherein a sacral fastener is advanced into the sacrum and positioned to abut the implant.

54. A method as in claim 43, wherein the procedure is minimally invasive.

55. A method as in claim 43, wherein the procedure is performed in a percutaneous manner.

56. A method as in claim 43, wherein a bone forming material is advanced through the area of bone penetration on the posterior surface of the sacrum and at least partially into the disc space that is immediately superior to the sacrum.

57. A method as in claim 43, wherein the implant contains an internal cavity adapted to house a bone forming material.

58. A method as in claim 43, wherein the first pathway extends along a first side of the sacral midline, wherein the facet joint formed by the interaction of the sacrum and the immediately superior vertebral bone is immobilized by a first fastener, wherein the immobilized facet joint is on the opposite side of the sacral midline from the first pathway.

* * * * *